United States Patent
Collins et al.

(10) Patent No.: US 6,495,140 B1
(45) Date of Patent: Dec. 17, 2002

(54) PROCESS FOR THE ISOLATION, RECOVERY AND PURIFICATION OF NON-POLAR EXTRACTIVES

(75) Inventors: F. William Collins; David A. Fielder; A. Bachir Sarr, all of Ottawa; Mark J. Redmond, Edmonton; Robert Z. D'Attilio, Ottawa, all of (CA)

(73) Assignee: Her Majesty in right of Canada as represented by the Minister of Agriculture and Agri-Food Canada (CA)

( * ) Notice: Subject to any disclaimer, the term of this patent is extended or adjusted under 35 U.S.C. 154(b) by 0 days.

(21) Appl. No.: 09/613,066

(22) Filed: Jul. 10, 2000

Related U.S. Application Data

(63) Continuation of application No. PCT/CA99/00003, filed on Jan. 8, 1999.
(60) Provisional application No. 60/071,251, filed on Jan. 12, 1998.

(51) Int. Cl.[7] .................. A61K 39/385; A61K 31/70
(52) U.S. Cl. .................. 424/195.1; 514/25; 514/783
(58) Field of Search .................. 424/195.1; 514/25, 514/783

(56) References Cited

U.S. PATENT DOCUMENTS

| | | | |
|---|---|---|---|
| 4,428,876 A | 1/1984 | Iwamura | 260/123.5 |
| 4,578,269 A | 3/1986 | Morein | 424/88 |
| 5,026,548 A | 6/1991 | Evans et al. | 424/195.1 |
| 5,057,540 A | * 10/1991 | Kensil et al. | 514/25 |
| 5,094,960 A | 3/1992 | Bonomo | 436/178 |
| 5,482,914 A | 1/1996 | Merle | 502/404 |
| 5,567,807 A | 10/1996 | Craig et al. | 530/395 |

FOREIGN PATENT DOCUMENTS

| | | | |
|---|---|---|---|
| DE | 2203884 | 8/1973 | |
| DE | 2549688 | 5/1977 | |
| DE | 3045910 | 7/1982 | |
| JP | 61036225 | 2/1986 | |
| JP | 62005917 | 1/1987 | |
| JP | WO92/06710 | 4/1992 | A61K/39/39 |
| WO | WO 96/38161 | * 12/1996 | |

OTHER PUBLICATIONS

Mizui et al. "Saponins from Brans of Quinoa, Chenopodium quinoa WILLD. I." Chen. Pharm. Bull., 36(4) 1415–1418, 1988.*

Fielder et al. "Isolation and Characterization of 4–Acetyl–benzoxazolin–2–one . . . " Tet. Letters 35, 521–524 (1994).

(List continued on next page.)

*Primary Examiner*—Ralph Gitomer
*Assistant Examiner*—Devesh Khare
(74) *Attorney, Agent, or Firm*—Heslin Rothenberg Farley & Mesiti P.C.

(57) ABSTRACT

A process is described for the isolation, recovery and purification of non-polar extractives using one or more extracting solvents from the group of lower alcohols, ketones, and water. The non-polar extractives may include one or more of the classes alk(en)lyresorcinols, steroid, triterpenoid and cardiac glycosides and saponins, steryl ferulates and other phenolic acid conjugates, flavoroids, polar lipids, alcohol-soluble antimicrobials, prolamines and other alcohol-soluble proteolipids complexes. The process uses an aliphatic-substituted polysaccharide gel matrix in a process of hydrophobic interaction chromatography, and involves the steps of absorption, washing and recovery, wherein the extractives are absorbed and desorbed in the presence of and as a result of the concentration and selection of the organic ste of regenerating the gel matrix for further use.

20 Claims, 11 Drawing Sheets

OTHER PUBLICATIONS

Fielder et al. "Total Synthesis of 4–Acetylbenzoxazolin–2–One" *J. Nat. Prod.* 58, 456–458 (1995).

Hjerten et al. "High–Perfomance Electrophoresis of Acidic and Basic Low–Molecular–Weight Compounds . . . " *J. Liquid Chrom,.* 12, 2471–2499 (1989).

Rippel et al. "Systematic method development in hydrophobic interaction chromatography" *J. Chrom.* 697, 17–29 (1995).

Gehas et al. "Isocratic hydrophobic interaction chromatography of dansyl amino acids" *J. Chrom.* 511, 123–130 (1990).

Onishi et al. "Isolation of Beer Foam Polypeptides by Hydrophobic Interaction Chromatography . . . " *J. Sci. Food Agric.* 65, 233–240 91994).

Haidacher et al. "Temperature effects in hydrophobic interaction chromatography " *Proc. Natl. Acad. Sci.* 93, 2290–2295 (1996).

* cited by examiner

Peak identification

1. Daidzin
2. Glycitin
3. Genistin
4. 6"- Malonyl daidzin
5. 6"- Malonyl glycitin
6. 6"- Acetyl daidzin
7. 6"- Malonyl genistin
8. 6"- Acetyl glycitin
9. Daidzein
10. 6"- Acetyl genistin
11. Glycitein
12. Genistein

ALKYL RESORCINOLS

C 17:0

C 21:1

PROCESS FOR THE ISOLATION, RECOVERY AND PURIFICATION OF NON-POLAR EXTRACTIVES

CROSS REFERENCE TO RELATED APPLICATIONS

This application is a continuation of copending PCT application CA99/00003, filed Jan. 8, 1999, which designated the United States and claimed the priority of U.S. application Ser. No. 60/071,251, filed Jan. 12, 1998. The priorities of both are claimed herein, and the entire disclosures of both are incorporated herein by reference.

The present invention relates to the isolation, recovery and purification of non-polar extractives. More specifically the present invention relates to the use of an aliphatic-substituted polysaccharide gel matrix in a process of hydrophobic interaction chromatography, for the absorption and desorption of the extractives in the presence of and as a result of the concentration and selection of an organic solvent.

BACKGROUND OF THE INVENTION

Agricultural plants, and waste streams from their processing, by way of an example, may contain components that are now being discovered as having desirable therapeutic and other benefits. For example: some saponins have been shown to exhibit antineoplastic chemotherapeutic value (U.S. Pat. No. 5,558,866), while others find, use in the treatment of hypercholesterolemia (U.S. Pat. No. 5,502,038). Still further antifungal (e.g. Crombie, W. M. L., and Crombie, L., Phytochemistry 25: 2069–2073, 1986) and immunogenic (U.S. Pat. No. 5,597,807) activities are known as well as surfactant, emulsifying and foam stabilizing properties which are summarized by Price et al. (CRC Crit. Rev. Food Sci. Nutr., 26, 27–135, 1987). These are but a few examples from the literature.

In addition, some flavones and their glycosides are known to exhibit antimutagenicity (e.g. Peryt, B., et al., Mutation Res. 269: 201–215, 1992), and antitumor activity (e.g. Wei, H., et al., Cancer Res. 50: 499–502, 1990). Further reports of beneficial biological activities and functional properties can be found in a number of reviews (e.g. "Plant flavonoids in biology and medicine II. Biochemical, cellular, and medicinal properties" Ed. By V. Cody, E. Middleton Jr., J. B. Harborne, and A. Beretz, Liss Inc, New York, 1988.)

Canadian Patent Applications 2,006,957 and 2,013,190 describe ion-exchange processes carried out in aqueous ethanol to recover small quantities of high value by-products from cereal grain processing waste. According to CA 2,013,190, an alcoholic extract from a cereal grain is processed through either an anionic and/or cationic ion-exchange column to obtain minor but economically valuable products. The anionic, cationic and neutral fractions were analysed by thin-layer chromatography and a number of components were identified. For example in an anionic fraction from an alcoholic extraction of hull-less whole oats, the following components were identified: phenolic acids, including ferulic acid, p-coumaric acid and caffeic acid; alkaloids such as avenanthramides; fatty acids, organic acids and amino acids. From the same alcoholic extract the neutral fraction contained compounds, such as: free sugars; phenolics, such as flavonoids; saponins such as avenacosides, and desglucosyl-avenacosides; alkaloids such as the avenacins; and various polar lipids. The compounds identified in the various fractions were not individually isolated by ion-exchange chromatography since many carried the same net charge under the conditions used and thus, this method alone is of little value in the isolation of these useful components for industrial or commercial use. Furthermore, the extractives to be isolated in the present invention are for the most part neutral under conditions used, and thus cannot be isolated by ion exchange chromatography alone, which sorts molecules according to charge.

PCT application WO 92/06710, discloses both the composition and isolation/separation technologies of Quillaja saponins for end uses as immunogenic complexes, using repeated semi-preparative HPLC on a reverse-phase column with an acetonitrile:water gradient elution. The scale of the separation appears not to be intended for production of significant quantities for commercialization but rather for proof of efficacy. The isolated products were produced only on the microgram scale. The scale-up of the separation technique for commercial applications was not disclosed.

U.S. Pat. No. 5,094,960 describes methods of removal of process chemicals from labile biological mixtures by hydrophobic interaction chromatography (HIC) using a resin comprising octadecyl chains coupled to a silica matrix. A method of removing lipid soluble process chemicals such as synthetic detergents, chemical inducers and organic solvents from aqueous biological fluids, particularly directed to producing a protein-containing composition such as blood plasma, cryoprecipitates, and blood plasma fractions, was described. In this disclosure materials and conditions are employed that minimize adsorption and separation of proteins and maximize the removal of the process chemicals. Substantially no biological material is retained on the column. Furthermore, no indication is given as to the intended field of use of any of the compounds and chemicals adsorbed in the process, nor specific conditions to selectively recover any of the adsorbed components retained on the column.

A number of different procedures are known for the isolation and purification of isoflavones. E. D. Walter described a procedure for the preparation of the isoflavone genistin and its aglycone genistein from defatted soybean flakes (J. Amer. Chem. Soc. 63, 3273–3276, 1941). The procedure involved methanol extraction, acetone precipitation, centrifugations and several recrystallizations and gave only one isoflavone, genistin, from which the aglycone genistein could prepared by acid hydrolysis. Ohta et al. described a procedure for isoflavone extraction from defatted soybeans wherein the flakes were extracted with ethanol and the ethanolic extract treated with acetone and ethyl acetate. Column chromatography of the ethyl acetate fraction on silica gel and Sephadex LH-20™ in several additional solvents produced a number of fractions from which individual isoflavones could be recovered by repeated recrystallization (Agric. Biol. Chem. 43: 1415–1419, 1979). Essentially the same separation protocols were used by Farmakalidis, E. and Murphy, P. A. to separate isoflavones extracted using acidified acetone rather than ethanol (J. Agric. Food Chem. 33: 385–389, 1985). These publications are but a few of the many examples in the literature for the laboratory scale extraction and purifications of specific isoflavones. However due to issues of solvent handling and disposal as well as economic feasibility, these procedures are hard to scale up to a commercial process and produce single compounds in undisclosed yields.

U.S. Pat. No. 5,679,806 addressed some of these issues, disclosing a process for the isolation and purification of isoflavones from plant material. The process consisted of three steps whereby the plant material is extracted, the resulting extract fractionated on a reverse phase low pressure polymethacrylate or $C_{18}$-substituted silica based chromatography column by gradient elution of the adsorbed isoflavones, and finally the resulting fractions containing specific isoflavones were eluted from the column. This process differs in several significant ways from the process described in the embodiments disclosed herein. First, the present process is not restricted to the isoflavone components but also yields a saponin fraction substantially free of isoflavones as well as the entire group of isoflavones which, if desired, can be further fractionated for individual components. Secondly, the present process does not rely on methacrylate or $C_{18}$-substituted reverse phase inorganic support matrices, which generally display much lower loading capacities and are harder to clean in place than polysaccharide-based gels. Thirdly, the flexibility of the present process allows that conditions be varied, either to capture the isoflavones by absorption or to allow them to elute through the column leaving other non- isoflavone components still absorbed, simply by varying the amount of water in an aqueous alcohol washing solution.

U.S. Pat. No. 5,482,914 teaches that agarose-based gels can be synthesized/modified for the binding of lipoproteins by covalently linking glycidyl ethers of polyoxyethylene detergents of the type HO—$(CH_2CH_2O)_n$—O—R to give a modified gel matrix suitable for the removal of lipoproteins from human and animal body fluids. This technology refers only to the chemical processes for producing the gel and makes no claims either for electrostatic binding of ligands such as we describe, or for any examples of separation or recovery from plant material.

Thus, there is still a need for processes, chromatographic procedures and improved absorption media that are adaptable to a wide range of compounds in a commercially viable manner that provide high concentrations of these compounds which can be subsequently recovered in high yield, purity and in unaltered form. There is also a need for a process in which the chromatographic media can be regenerated and re-used many times to reduce both replacement costs and waste disposal. Furthermore, for commercial scale production of non-polar extractives it would also be advantageous to reduce the direct contact of solvents such as chlorinated hydrocarbons (e.g. chloroform, dichloromethane), nitriles (e.g. acetonitrile), aromatics (e.g. benzene, toluene), other potentially undesirable reagents (e.g. salts, mineral acids, bases), and chromatographic media contaminants (methacrylate-, divinylbenzene-, styrene-monomers, silica etc.) from direct contact with desired products. It is to these ends that this technology is directed.

SUMMARY OF THE INVENTION

The present invention relates to a process for the isolation, recovery and purification of non-polar extractives or amphiphiles, prepared using one or more extracting solvents, using an aliphatic-substituted polysaccharide gel matrix. More specifically the gel matrix is a covalently-linked, alkyl-substituted neutral polysaccharide gel matrix. The present invention relates to the use of these gels for the absorption and desorption of the extractives in the presence of and as a result of the concentration and selection of an organic solvent in a process of hydrophobic interaction chromatography.

Thus, according to the present invention there is provided a method of isolating a non-polar extractive comprising: contacting said non-polar extractive in an aqueous organic solvent solution with an aliphatic-substituted polysaccharide gel matrix; washing said gel matrix with said aqueous organic solvent solution, washing said gel matrix with an additional aqueous organic solvent solution, wherein the proportion of the organic solvent in said additional solution is increased; and recovering said extractive from an effluent stream.

In one embodiment of the present invention the gel matrix is a neutral polysaccharide gel matrix of the polyanhydrogalactan class, a neutral polysaccharids gel matrix of the polydextran class or a neutral polysaccharide gel matrix of the hydroxypropyl polydextran class.

In a further embodiment the gel matrix contains covalently linked alkyl substitution of from 4 carbon (i.e butyl) to 8 carbon (ie octyl) functions at a 4% or more substitution rate, stable in neutral and mildly acidic or alkaline solutions of said aqueous organic solvent solution, with a molecular size exclusion cut-off range equal to or greater than 10,000 Daltons.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1A:
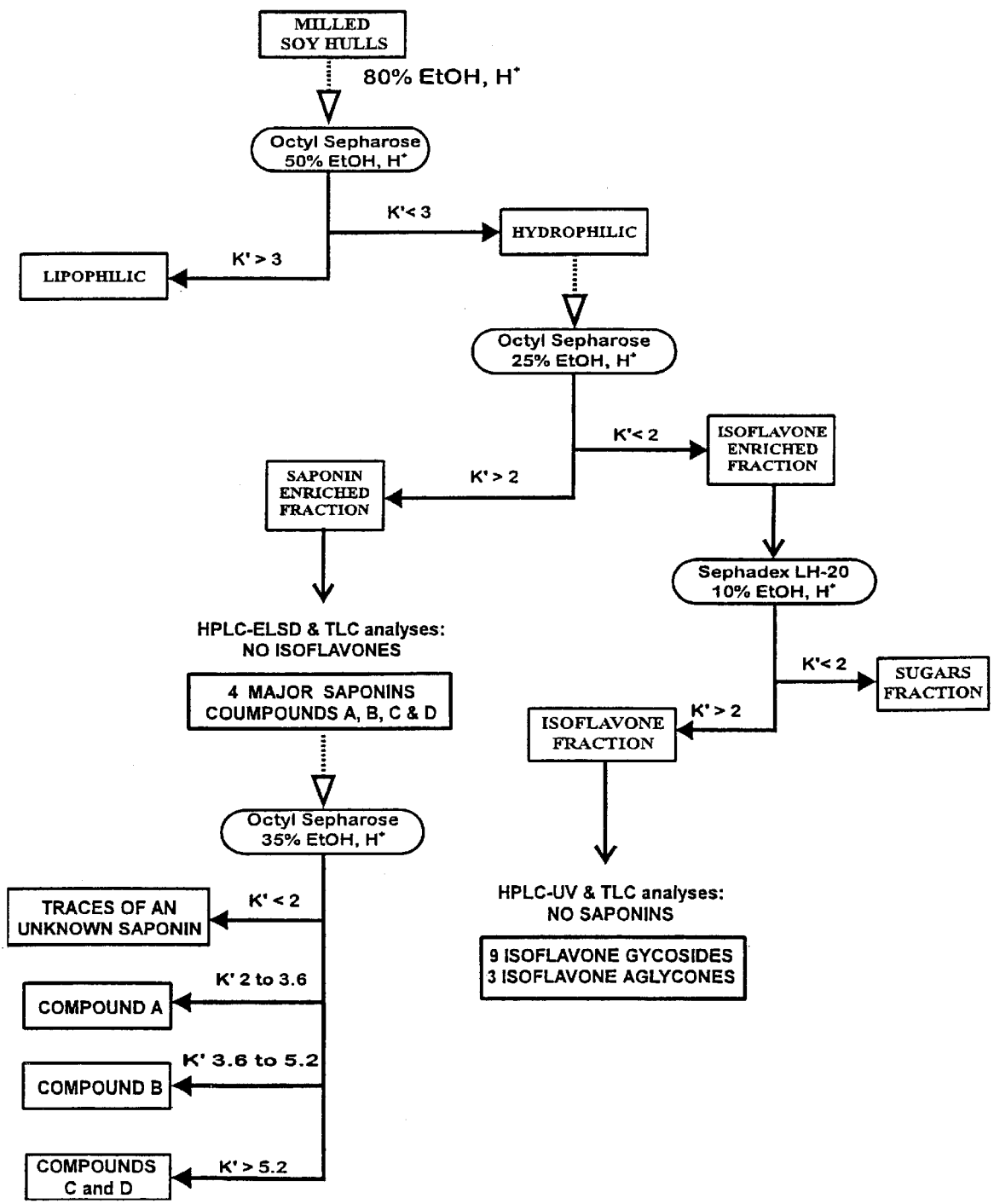
FIG. 1A shows the group separation and purification scheme of isoflavones and saponins, and the purification of individual saponins from soy hulls. The HPLC analysis of the isoflavone fraction is shown in FIGS. 1B and 1C.

The present invention relates to a process for the isolations, recovery and purification of non-polar extractives, prepared using one or more extracting solvents, using an aliphatic-substituted polysaccharide gel matrix. The present invention relates to the use of these gels for the absorption and desorption of the extractives in the presence of and as a result of the concentration and selection of an organic solvent.

The fundamental principles of both hydrophobic interaction chromatography (HIC) and reverse phase chromatography (RPC) are similar: chromatographic separation of components of a mixture based on their differential affinities between a non-polar or hydrophobic ligand attached to a stationary phase, and a mobile phase. In RPC, the stationary phase usually, but not always, consists of an inorganic, pelliculate or particulate, hydrophilic support, typically silica, onto which a specific ligand with a relatively high degree of hydrophobicity has been introduced at a complete or extremely high substitution rate to effectively replace, mask or resurface the hydrophilic stationary phase. The mobile phase usually, but not always, contains an organic modifier (i.e. organic solvent) typically methanol, acetonitrile, or tetrahydrofuran. In HIC, the stationary phase typically consists of an organic, hydrophilic, macroporous support, typically a chemically modified polysaccharide or polyacrylamide, onto which a specific ligand with a relatively low degree of hydrophobicity, has similarly, but usually to a much lower substitution rate, been introduced to modify but not necessarily eliminate the hydrophilic properties of the support. The mobile phase usually, but not always, consists of water containing a buffer or salt solution of variable concentration.

RPC is now the most commonly used technique for high performance liquid chromatography (HPLC) separation of low molecular weight, relatively stable organic compounds. However, separation of many biological macromolecules (e.g. proteins, peptides and nucleic acids) by RPC has found only limited application, because the stronger interaction with a highly hydrophobic stationary phase and the use of organic solvents as eluent constituents can be very detrimental to the native structure of the macromolecules. As a result of these interactions, most of the macromolecules are subjected to unfolding and denaturation with the concomitant loss of some or all of their biological activity.

HIC has developed as a practical alternative to RPC for the separation and purification of biological macromolecules because both the absorption and desorption precesses can be carried out in an aqueous buffer by simply varying the salt concentrations, conditions that are more favorable to the retention of biological activity of the macromolecule. However, few applications of HIC for the separation of low molecular weight, relatively stable organic compounds appear to have been made. In accordance with the present invention, by maintaining a functional hydrophilic core in addition to the hydrophobic ligand in close spacial proximity, the HIC stationary phase displays unique advantages for the separation and purification of amphiphiles (i.e. compounds containing both hydrophilic and hydrophobic regions) not available in most if not all RPC stationary phase chromatographic media. Examples of such amphiphilic extractives, include but are not limited to saponins, flavonoids and prolamines, which contain hydrophilic substituents (i.e. glycosidic residues) attached to a relatively non-polar backbone. If these amphiphiles additionally show stability towards certain organic. solvents such as the lower alcohols and ketones, including ethanol, isopropanol and acetone, these solvents can be used to recover the components bound to the gel (i.e. running the HIC system in "RPC mode") by either gradient, sequential or batch recovery techniques known by the skilled person in the art of chromatography.

Furthermore, according to the present invention we have observed that such HIC gels possess the capacity to clarify aqueous dispersions and micelles known to be formed when such amphiphiles (i.e. aqueous solutions and dispersions of saponins, flavonoids and prolamines above their critical micellar concentration) are produced artificially or encountered in the extraction, concentration and purification or other manipulation of aqueous alcoholic preparations from agricultural plants and co-processing streams.

The present invention depends on the hydrophobicity of the non-polar extractives to be isolated and the change in hydrophobicity that results from altering the concentration of the recovery solvents, which can be achieved by adding more or less water to the recovery solvent. More specifically, the present invention is based on the observed selective differences in the hydrophobic attraction between relatively non-polar extractives containing aliphatic and/or alicyclic functional groups, as compared to those containing aromatic and/or olefinic functional groups, or neither; and an aliphatically-substituted polysaccharide-based insoluble gel; and on the changes in this attraction that can be made by altering the composition of suitable solvents, simply by the addition of more or less water.

By non-polar extractives, it is meant that the extractives are only partially soluble in aqueous alcoholic solvents ranging in composition from 5% to 95%. This term includes extractives that are relatively non-polar. In one aspect of the present invention the groups of compounds that can be separated are non-polar compounds and are selected from the group, but are not limited to: steroids and triterpenoids, such as saponins, cardiac glycosides and steryl conjugates; flavonoids, such as flavones, flavonols, isoflavones and all of their glycosides; phenolic conjugates, such as aliphatic alcohol, esters and amides; polar lipids, such as mono- and di-glycerides and their derivates and alk(en)ylresorcinols; and prolamines, such as zein, avenin, hordein or gliadin. The non-polar compounds of the present invention include both naturally occurring compounds and synthetic compounds.

By synthetic compounds it is meant any compound prepared by synthetic chemical means. The method of the present invention is particularly useful for the purification of synthetic compounds which have pharmaceutical or therapeutical value.

Naturally occurring compounds include the compounds referred to above, and also include compounds from algae, fungi and unicellular organisms. These naturally occurring compounds include compounds naturally occurring in the microorganism and also those produced by genetically altered cells.

In one embodiment of the present invention, the process is used to isolate soyasaponins. Soyasaponins are sapogenols (triterpenoid aglycones) containing up to five sugars and in some cases have a terminal moiety, tri or tetra acetylated. Saponins in general and soyasaponins in particular are gaining much attention because of the growing market share of soybeans. Soyasaponins have been reported to exhibit haemolytic, goitrogenic, antioxidative and hypolidemic properties. They have also been shown to impart a bitter and astringent taste to soy-based foods. Their isolation and characterisation is important for the breeding of new varieties and for their production as pharmacologically active value-added products. However, because of. their complex chemistry, known chemical isolation techniques (i.e., saponification or solvent extraction) may yield low quantities or hydrolysed products. Other examples of useful saponins include the saponins from ginseng and quinoa. Quinoa saponins have demonstrated to be immune system stimulants (U.S. Pat. Nos. 5,597,807 and 5,688,772).

In a further embodiment of the invention, the process is used to isolate steryl ferulates. Steryl ferulates are naturally occurring ferulic acid esters of plant sterols (i.e. modified triterpene alcohols). They have been identified in the bran oil fraction of a number of monocot cereal grains including wheat, rye, triticale, corn, and rice (e.g. Norton, R. A., Cereal Chem.71: 111–117 1994, and references cited therein). In the oil derived from rice bran, the mixture of steryl ferulates is known as oryzanol or γ-oryzanol and constitutes from about 1.5 to 2.9% of the total oil composition. The ability of this mixture to reduce serum cholesterol has been reported (Lees, A. M., et al., Atherosclerosis 28: 325–338, 1977; Rong, N., et al., Lipids 32: 303–309, 1997). Processes for its extraction from rice bran oil have been patented (e.g. Takeshi, Y., "γ-oryzanol" German patent #1,301,002 Aug. 14, 1969, Chem. Abstr. 71: 128704r, 1969; Hishashi, S., "Highly concentrated separation of oryzanol by two-step alkali treatment" Japanese patent #76,123,811 Oct. 28, 1976, Chem Abstr. 86: 104664m, 1977). Patents for its formulation (e.g. U.S. Pat. No. 4,612,187) and use in reducing serum cholesterol (U.S. Pat. No. 5,514,398; PCT/EP/96/02344) and in sunscreen formulations (e.g. U.S. Pat. No. 5,817,299) are also known. In the production of oryzanol, solvent extraction, physical refinement and alkali treatment stages lead to mixtures of varying composition due to the crudeness of the process and the complexity of the naturally occurring mixture. From pharmaceutical and therapeutic standpoints, a more definitive isolation, purification and validation system is clearly needed before the biochemical basis of these effects can be better understood.

In one embodiment of the present invention, the compounds can be isolated from plant material. The term plant material includes products of agriculture, viniculture, horticulture or aquaculture. Agricultural plants include cereal grains, for example wheat, oats, rye, corn, rice, quinoa, amaranth, buckwheat, triticale or barley; or oilseeds, such as soybean, canola, flaxseed, sunflower, safflower or mustard; or pulse-crops, for example, peas, lentils or. beans; or forage crops, such as fescue, timothy, clover, alfalfa or wheatgrass; or herbs, such as parsley, rosemary, sage, or mint. The compounds can also be recovered from their co-processing streams. The method of the present invention can also be used for the clarification and stabilization of alcohol-water dispersions of cereal and oilseed lipid/protein hazes. However, the invention is not limited to compounds isolated from plants or agricultural co-processing products. The invention can also be used to extract compounds from algae, fungi and unicellular organisms.

The washing solvents, extracting solvents, or recovery solvents, in the context of the present invention these terms are interchangeable, can include but are not limited to the lower alcohols such as methanol, ethanol, propanol or isopropanol; ketones, such as acetone; water, and a combination of the lower alcohol, or ketone, with water.

A person skilled in the art of extraction of naturally-occurring plant constituents will recognize that a number of different extractions methods exist in the literature, including percolation, vat extraction, counter-current extraction, etc. The particular method of extraction used is not important to the process of the present invention.

The present invention uses hydrophobic interaction chromatography alone or in combination with other separation techniques to isolate the compound of interest. In this respect, the invention defined in the present application can be combined with the separation techniques defined in Applicant's co-pending application entitled "The Preparation of Novel Gels for the Purification of Non-Polar Extractives", which uses electrostatically-linked, aliphatic- or alicyclic-substituted anionic or cationic polysaccharide gels prepared from macroporous ionic polysaccharide chromatographic media.

In one embodiment of the present invention the aliphatic-substituted polysaccharide gel matrix typically consist of a neutral polysaccharide of the polyanhydrogalactan class such as cross-linked agarose containing covalently linked alkyl substitution of from 4 carbon (ie butyl) to 8 (ie octyl) carbon functions preferably at 4% or more substitution rate, stable in neutral and mildly alkaline solution of the aqueous organic solvent with a molecular size exclusion cut-off range equal to or greater than 10,000 Daltons.

For example suitable gels include Octyl-Sepharose CL-4B™ and Butyl-Sepharose™ (Amersham Pharmacia Biotech, Piscataway, N.J.).

The neutral polysaccharide gel matrix of the present invention can also include a gel of the hydroxpropyl polydextran class.

The process of purifying the non-polar extractive, according to the present invention involves three basic steps: absorption, washing and recovery. According to one aspect of the present invention, the process involves a fourth-optional step of regenerating the column, without the use of a harsh chemical treatment or the generation of excessive salt or non-recoverable processing waste stream.

According to the present invention, separation and purification of a wide range of extractives with similar solubilities in aqueous alcoholic solvents can be effected based on their differential binding to specifically-modified polysaccharide gels. Such extractives can include: steroids and triterpenoids, such as saponins, cardiac glycosides and steryl conjugates; flavonoids, such as flavones, flavonols, isoflavones and all of their glycosides; phenolic conjugates, such as aliphatic alcohol, esters and amides; polar lipids, such as mono- and di-glycerides and their derivates and alk(en)ylresorcinols; and prolamines, such as zein, avenin, hordein or gliadin.

In the case of soybean processing waste, the non-polar extractives consisted of, amongst others, both saponin and isoflavone derivatives which were freely solubilized under the extracting conditions and solvent used. The mixture of saponins present includes at least 4 components consisting of at least one aglycone (no sugars) and 4 glycoside derivatives, as revealed by thin-layer and high performance liquid chromatography, and the mixture of isoflavones consists of at least 12 components consisting of at least 3 different aglycones (no sugars) and at least 9 glycoside derivatives of these aglycones as revealed by thin-layer and high performance liquid chromatography, diode array UV spectroscopy, and mass spectrometry. Even though both classes of natural extractives display similar solubilities in the solvents used, and contain glycosylated and non-glycosylated derivatives, and even though the glycosidic component of both classes in some cases consists of the same sugars; the two classes of natural extractives are clearly separated on the chromatographic gel based on intrinsic differences in their relative attraction or binding to the gel under the conditions used. From similar examples derived from the practice of the invention, it has been established that, due to the preferential retention of compounds containing aliphatic/alicyclic functional groups (i.e. saponins) over those containing aromatic/olefinic functional groups (i.e. flavonoids) at comparable degrees of glycosylation, a separation of the two groups is possible. In practice, the relative preferences and working ranges using an octyl-substituted gel matrix and aqueous ethanol solvent systems have been found, but are not limited to be, as summarized below in Table 1.

TABLE 1

Relative selectivity and working ranges for separation of saponin and flavonoid derivatives on Octyl Sepharose CL-4B ™

| Relative Non-Polarity (Hydrophobicity) | Type and Relative Retention | | Range of Solvent EtOH:H$_2$O (Vol:Vol) |
|---|---|---|---|
| | Retained | Not Retained | |
| + | | Saponin tetra-, penta-, and hexaglycosides | 0:100 to 10:90 |
| ++ | Saponin triglycosides | | 10:90 to 25:75 |
| +++ | Saponin monoglycosides and diglycosides > | Isoflavone and flavonol monoglycosides and diglycosides | 25:75 to 50:50 |
| ++++ | Saponin aglycones (i.e. sapogenins), sterols, steryl ferulates, alk(en)yl-resorcinols > | Isoflavone, flavone, and flavonol aglycones, phenolic acids and their amides | 50:50 to 95:5 |

In Table 1, the workable range values are reported as two suitable solvent proportions: the first, for the sorption and washing steps, and the second is the upper range needed for the recovery step. As can be seen in the table, the workable ranges depend on the degree of glycosylation of components being separated but between groups of comparable degree of glycosylation (aglycones, monglycosides, diglycosides, etc.) those containing aliphatic/alicyclic functions (i.e. saponins, sterols, alk(en)ylresorcinols) are preferentially retained by the Octyl Sepharose CL-4B™ gel over those containing aromatic functionality. The proportion of solvent, for example ethanol in the elution solvent solution used for various working ranges increases as the hydrophobicity increases to ensure all components in the mixtures remain soluble, and because less water is needed to effect binding of the compounds to the gel.

Amongst the glycolipids, based on the relative affinities observed in "reverse phase mode of HIC", the order of increasing binding (i.e. requiring less water in the recovery solvent stage) will be diglycosyl monoglycerides~dimonoglycosyl monoglycerides<monoglycosyl monoglycerides<diglycosyl diglycerides<monoglycosyl diglycerides<<monoglycerides<<diglycerides<<triglycerides.

In establishing whether a compound is considered to be bound to the gel and to have exhibited hydrophobic interaction with the gel, the following citeria must be met:
a) it must be soluble in, or form a micelle or stable emulsion in, the solvent with which it is loaded onto the column, and with which the column is washed; and
b) it must be retained by the gel after washing with at least 1.25×V$_b$ of the washing solvent, wherein V$_b$ is the packed bid volume of the column; wherein the washing solvent is a lower alcohol in combination with water in a ratio sufficient to retain said compound.

This latter criterion must be met since porous gels of the types described herein show molecular size exclusion capabilities. These effects are not however observed beyond approximately 1.25×V$_b$ and therefore are not involved in the processes or practices described.

In the recovery step, the proportion of the organic solvent in the aqueous organic solvent solution is increased to decrease the hydrophobic binding of the extractive to the gel and thus elute the extractive. In some embodiments the extractive could be eluted with the initial washing steam.

In the present invention, reference will be made to the degree of relative hydrophobic interaction of specific compounds or groups and/or classes of compounds by the use of a dimensionless constant, K' defined as the ratio of the number of mL of a particular solvent required to move the compounds through a volume of 1 mL of gravity packed gel. Since this dimensionless constant is independent of column dimensions (i.e. length, diameter, etc.), the conditions described herein can be used for scaled up operations over several magnitudes.

As noted previously, as optional fourth step of the present invention is the regeneration of the column, without the use of any harsh chemicals or the generation of excessive salt or non-recoverable processing waste stream. Since conditions for each application have been established wherein the compounds of interest have been totally removed from the gel, the column can be regenerated and re-equilibrated in the starting solvent. Surprisingly, it has been found that a simple washing of the gels with a suitable solvent such as 95% ethanol or isopropanol is sufficient in most cases to remove any material appearing to be adhering to the gels at the end of a process application. The gels are then re-equilibrated with starting solvent for immediate re-use. In this manner, regeneration and recycling up to at least 4000 times over 10 years have been observed without noticeable loss of effectiveness in the processes described herein. Clean-in-place/sanitation procedures where deemed appropriate can be effected using dilute NaOH as per manufacturers recommendations (Amersham Pharmacia Biotech manuals, technical bulletins, etc.).

The purification of the compound, according to the present invention, can be carried out at any suitable temperature, known to persons skilled in the art. The column separations can be accomplished at temperatures ranging from about 2° C. to 60° C. Temperature ranges from about 4° C. to 30° C. being more commonly used.

While this invention is described in detail with particular reference to preferred embodiments thereof, said embodiments are offered to illustrate but not to limit the invention.

EXAMPLES

Example 1

Isolation of Soyasaponins and Isoflavones from Soy Hulls Using Hydrophobic Interaction Chromatography on Octyl Sepharose CL-4B™

Soybean hulls (Glycine max L., selection lines OT93-26 and OT93-28) were finely ground and 25 g samples added with vigorous stirring to 125 mL (solids/liquid=1/5) refluxing acidified aqueous 80% ethanol (ethanol:water:glacial acetic acid 80:19:1 v:v:v), and heated for 20 additional minutes with continuous stirring under reflux. After cooling to approximately 4° C., the resuspended mixture was transferred to a volumetrically graduated glass column fitted with a coarse porosity fritted disk, and allowed to warm to room temperature (25° C.) and settle by gravity to give a packed bed of known volume (V$_b$). The column was then drained and washed with 2×V$_b$ fresh acidified aqueous 80% ethanol, and the extraction repeated twice.

After draining, the solid residues were removed and air dried to constant weight to determine the percentage of material extracted. The combined extracts were reduced to an oily syrup in vacuo by rotary evaporation at 40° C.

Hydrophobic interaction chromatography on Octyl Sepharose CL-4B™ was utilized to achieve both group separation of the soysaponins and fractionation/purification of individual soysaponins.

Group separation of the soysaponins from non-saponin, co-extracted glycerides, pigments, flavonoids, amino acids, peptides, and sugars amongst others, was carried out by first, dispersing the oily syrup in 80% ethanol, adding 5 mL of Octyl Sepharose CL-4B™ beads in 80% ethanol and evaporating the mixture to a thick slurry in vacuo by rotary evaporation at 40° C., resuspending the mixture in acidified aqueous 50% ethanol (ethanol:water:glacial acetic acid 50:49.9:0.1 v:v:v), and transferring the slurry to a graduated column of 45 mL $V_b$ Octyl Sepharose CL-4B™, pre-equilibrated in the acidified aqueous 50% ethanol solvent. The column (final $V_b$ 50 mL) was then washed with $3 \times V_b$ of the same solvent, to give a washing fraction with $K' \leq 3$, containing the saponins and isoflavones amongst others, and a $K' \geq 3$, still hydrophobically bound to the gel. This $K' \geq 3$ fraction, containing carotenoid pigments, acyl glycerides, free phytosterols, and others, can be recovered and the gel recycled by first passing $2 \times V_b$ of 95% ethanol to recover the bound material, and then $2 \times V_b$ of re-equilibrating solvent. The $K' \leq 3$ fraction was further fractionated on the same column of Octyl Sepharose CL-4B™, pre-eqilibrated in acidified aqueous 10% ethanol (ethanol:water:glacial acetic acid 10:89.9:0:1 v:v:v) by repeating the above procedures of concentrating the $K' \leq 3$ fraction, adsorbing the fraction to the column and washing the column with $2 \times V_b$, except the solvent was acidified aqueous 25% ethanol. The column was pre-equilibrated in acidified aqueous 10% ethanol rather than acidified aqueous 25% ethanol to minimize any chromatographic flow problems arising from density difference between the concentrated sample and the gel. This procedure gave a $K' \leq 2$ fraction containing all the isoflavones and other components, but devoid of saponins, and a $K' \geq 2$ fraction hydrophobically bound to the gel containing all the saponins amongst others but devoid of isoflavones. This saponin-enriched $K' \geq 2$ fraction was recovered simply by increasing the ethanol content of the washing solvent from 25% to 80% (i.e. to decrease the hydrophobic binding of the saponins to the gel) and washing the column with $2 \times V_b$ of acidified aqueous 80% ethanol. The entire extraction, group separation and purification scheme is shown in FIG. 1a. The completeness of this isoflavone/saponin group separation and the identity of the major components of these groups was confirmed by thin layer chromatography (TLC), high performance liquid chromatography (HPLC) and mass spectrometry (MS) analyses of these two fractions using the following protocols.

Thin-Layer Chromatography (TLC)

TLC of saponins was performed on MKC$_{18}$F reversed phase plates (1×3 in., 200 μm thickness from Whatman International Ltd, Maidstone, England) developed with methanol: aqueous 5% acetic acid (75:25 v:v). Compounds were visualised by spraying with a 0.5% solution (v:v) of p-anisaldehyde in acidified aqueous ethanol (ethanol concentrated sulfuric acid:water:p-anisaldehyde 90:5:4.5:0.5 v:v:v:v) and heating at 100° C. for 3 min. This reagent gives a number of distinct colors with different constituents including brown (free sugars), transitory yellow quickly turning to pink, green, or grayish-blue (saponins), slowly appearing reddish (amino acids, prolamines), purple (galactosylglycerides), and yellow (lysophosphatides). TLC of isoflavone aglycones and glycosides was carried out on 200 μm thick silica gel plastic-backed plates (Baker-Flex 1B-2-F, VWR Scientific, Ottawa, Canada) using the following solvent systems: for aglycones, toluene:methyl ethyl ketone:acetic acid (80:15:5 v:v:v); for glycosides, dichloromethane:ethyl acetate:methanol:aqueous 5% acetic acid (40:35:20:5 v:v:v:v). Detection was made using a spray reagent consisting of 0.1% (w:v) diphenylborinic acid ethanolamine complex (Sigma Chemical Co., St. Louis, Mo.) in isopropanol and examining the air-dried plate in UV (365 nm) light.

High Performance Liquid Chromatography (HPLC)

HPLC analysis of saponins was conducted using a Thermo Separation Products solvent delivery system and data collection software (PC 1000), a $C_{18}$ CSC HyperSil column 120 Å, 5 μm, (250×4.6 mm) operated at a temperature of 25° C., an Alltech Varex MKIII evaporative light scattering detector (ELSD) with the drift tube temperature set at 120° C. and the gas flow at 3.06 SLPM. The solvent system consisted of acetonitrile, water and aqueous 5% glacial acetic acid:

| Time | Acetonitrile | H$_2$O | 5% acetic acid |
|---|---|---|---|
| 0 | 36 | 57.8 | 6.2 |
| 20 | 36 | 57.8 | 6.2 |
| 25 | 48 | 47 | 5 |
| 30 | 48 | 47 | 5 |
| 35 | 100 | 0 | 0 |
| 40 | 100 | 0 | 0 |
| 45 | 36 | 57.8 | 6.2 |

The flow rate was 1 mL/min.

HPLC analysis of isoflavones was performed using the same column and solvent delivery system but using a Waters 991 photo-diode array UV spectrophotometric detection system (262 nm) and accompanying software. The following solvent system was used at a rate of 1 mL/min:

| Time | Methanol | 2% Acetic Acid |
|---|---|---|
| 0 | 30 | 70 |
| 30 | 55 | 45 |
| 40 | 90 | 10 |
| 45 | 100 | 0 |
| 50 | 100 | 0 |
| 55 | 30 | 70 |

Figure 1B:
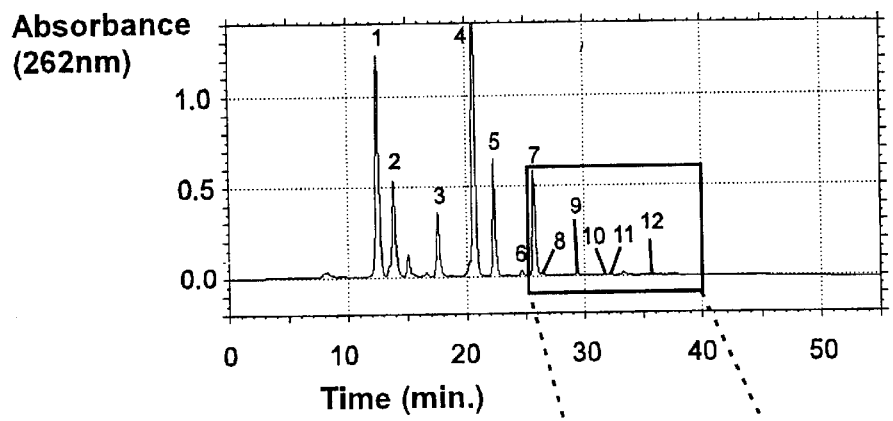

The results are shown in FIG. 1b.

Mass Spectrometry (MS)

Tandem Liquid Chromatography-Mass Spectrometry (HPLC-MS) analyses of pure compounds were performed using flow injection (FIA) with no column. The mobile phase consisted of methanol:water (70:30) and the flow rate was 100 μL/min. Solvents were delivered using a Hewlett Packard 1100 binary pump. Mass spectrometry analyses were conducted using a Micromass Quattro Spectrometer with an upgraded hexapole source operating in both electrospray positive and negative modes. Scanning was done in the range of 200 to 1500 m/z units with a cone voltage of 100 or 220 Volts.

The purification of individual saponins from the saponin-enriched $K' \geq 2$ fraction was also carried out by hydrophobic interaction chromatography on a 150 mL glass column with a bed volume of 100 mL of Octyl Sepharose CL-4B™ using isocratic elution with acidified aqueous 35% ethanol. Compound A possessed a K' value range from 2 to 3.6 and compound B from 3.6 to 5.2. The entire extraction, group separation and purification scheme is summarized in FIG. 1a.

The acidified aqueous ethanol extraction yielded 14% of solubles from soybean hulls. Passage through an Octyl Sepharose CL-4B™ gel with acidified aqueous 50% ethanol separated highly non-polar components such as fats, carotenoid pigments and phosphatides, from the saponins, flavonoids and other more polar components. Further enrichment of the saponin fraction was performed with acidified aqueous 25% ethanol on the same gel, with highly polar compounds eluting with $2 \times V_b$ bed volumes leaving the fraction of interest on the column. A third level of purification was performed on QAE Sephadex A-25™ in the acetate form and the fractionation of individual saponins was conducted on Octyl Sepharose CL-4B™ with acidified aqueous 35% ethanol.

Thin layer chromatography analysis of fractions showed 4 distinct spots labelled A, B, C and D. HPLC analysis of fractions showed a peak at 7 min in the fraction with K'<2, peak A and a minor peak not previously detected on TLC and appropriately labelled unknown in K'2–3, peak A and B in K'3–4, peak B and remnants of peak A in K'4–5 and peak C and D in K'>5.

Mass spectrometry positive ion flow injection analysis (FIA) of a purified compound B fraction showed ion peaks at m/z 943, 965 and 987 as $[M+H]^+$, $[M+Na]^+$ and $[M+2Na]^+$. Negative ion FIA showed a quasi-molecular ion peak at m/z 941. These ions indicated a compound with molecular weight of 942 corresponding to soyasaponin Bb reported by Shiraiwa et al. (Shiraiwa, M., et al., Agric. Biol. Chem. 55, 911–917, 1991) and soyasaponin I by Fuzzati et al. (J. Chromatography A. 777, 233–238, 1997). Soyasaponin I was renamed soyasaponin Bb by Shiraiwa et al. The presence of the major ions reported by Fuzzati et al. with m/z 459, 599, 617, 635, 797 was confirmed. Compound B would then be described as soyasaponin Bb. In addition, compound A was confirmed to be soyasaponin Ba (Shiraiwa et al.) by comparison of TLC and HPLC behaviour with an authentic sample.

Figure 1C:
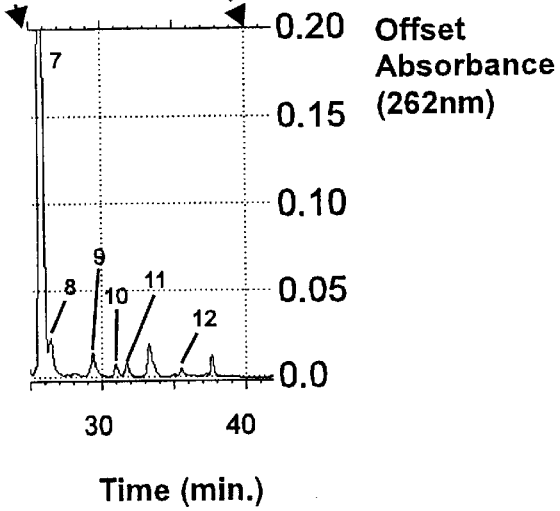

The isoflavone-enriched fraction was prepared for HPLC analysis by treatment with Sephadex LH-20™ as follows: The fraction was evaporated in vacua to a thick syrup by rotary evaporation at 40° C., taken up in acidified aqueous 10% ethanol (ethanol:water:glacial acetic acid 10:89.9:0.1 v:v:v), and added to a graduated column of 50 mL Sephadex LH-20™, pre-equilibrated in the acidified 10% aqueous ethanol solvent. The column was then washed with $2 \times V_b$ of the same solvent, to give a washings fraction with K'≦2, containing the sugars, organic acids and amino acids amongst others, and a K'≧2 fraction, containing the isoflavones, which was recovered from the gel by washing with $2 \times V_b$ of 80% ethanol. This isoflavone fraction was then used for HPLC analysis. As shown in FIGS. 1B and 1C, the isoflavone fraction contained at least 12 distinct isoflavones of known structure, identified by comparison of TLC, HPLC, and UV spectra with published data (see Wang, H., and Murphy, P. A.,J. Agric. Food Chem. 42: 1666–1673, 1994; Barnes, S., et al. J. Agric. Food Chem. 42: 2466–2474, 1994), along with a number of other peaks all of which showed spectral properties typical of isoflavones.

Example 2

Isolation of Soyasaponins from Soy Flour Using Hydrophobic Interaction Chromatography on Octyl Sepharose CL-4B™

Figure 2:
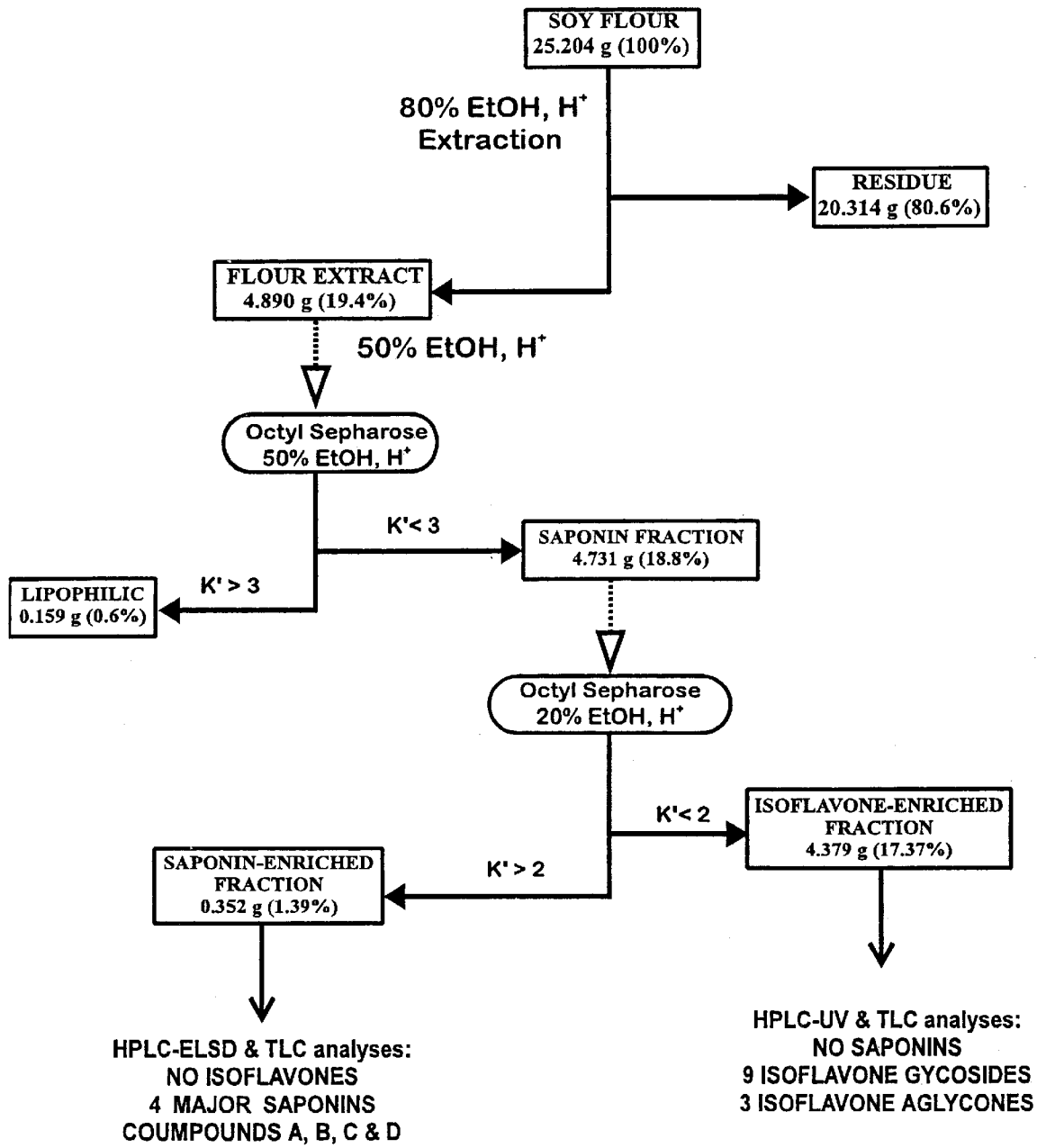
FIG. 2 is the purification process of saponins from soy flour.

Twenty five g soy flour (Type I, not roasted, defatted, Sigma Chemical Co., St Louis, Mo.) was added with vigorous stirring to refluxing 80% aqueous etnanol containing 1% glacial acetic acid and extracted, concentrated and fractionated by hydrophobic interaction chromatography on Octyl Sepharose CL-4B™ using essentially the same procedure as described in Example 1 except that the final group separation of soysaponins was carried out in acidified aqueous 20% ethanol as opposed to 25% ethanol used in Example 1. The isolation scheme is summarized in FIG. 2.

Thin layer chromatography and HPLC analyses were performed as in Example 1.

The acidified aqueous ethanol extraction yielded 19.4% (dry basis) of solubles from the soybean flour. As in Example 1, passage through an Octyl Sepharose CL-4B™ gel with acidified aqueous 50% ethanol separated highly non-polar components such as fats, carotenoid pigments and phosphatides (0.63% dry basis), from the saponins, flavonoids and other more polar components to yield a saponin-enriched fraction (18.77% dry basis). Further enrichment of the saponin fraction was performed with acidified aqueous 20% ethanol on the same gel, with highly polar compounds eluting with $2 \times V_b$ (17.37% dry basis) leaving the fraction of interest on the column. This fraction was then recovered using 80% ethanol containing 0.1% glacial acidic acid (1.39% dry basis). TLC and HPLC analyses performed on these fractions showed the soysaponin fraction to contain essentially the same components as those revealed in Example 1.

Example 3

Isolation and Purification of Digitonin from an Artificial Source by Hydrophobic Interaction Chromatography as an Example of the Recovery of a Drug from an Agricultural Crop which has been Genetically Transformed to Produce Pharmaceuticals.

Digitonin is a cardiac glycoside produced by Digitalis purpurea L. (Foxglove, Scrophulanraceae). In modern medicine, digitonin is used to increase the force of the systolic contractions and to prolong the duration of the diastolic phase in congestive heart failure. The generic name is digitonin and the trade name Crystodigin™. It belongs to the drug class of cardiac glycosides Merck Index #3204, E. Merck, 12th Edition, 1996). The Merck Index describes the content of the commercial product as 70 to 80% digitonin, 10 to 20% gitonin and tigonin, and 5 to 10% minor saponins. The aglycone of digitonin is described as digitogenin [(25R)-5α-Spirostan-2α,3β,15β-triol], and the aglycone of gitonin is described as gitogenin [(25R)-5α-Spirostan-2α, 3β-diol]. The aglycone of tigonin is tigogenin [(25R)-5α-Spirostan-3β-ol]. Digitonin and tigonin have 2 glucosyl, 2 galactosyl and one xylosyl residues while gitonin has 2 glucosyl, 1 galactosyl and one xylosyl residues. Thus digitonin and tigonin are pentaglycosides and gitonin is a tetraglycoside.

Although digitonin occurs in Digitalis purpurea L. and is normally extracted and purified from extracts of the aerial parts of this plant, the use of genetically modified plants for the production of this drug represents an alternative that may prove economically more practical (from the standpoints of ease of cultivation, yield, storage, transport, etc.) than current practices. It is not the purpose of the current example to provide an economically practical alternative to these practices, but rather to illustrate the application of the technology described herein for the isolation and purification of the drug from model sources. To this end, the alternative model plant matrix system chosen was a cereal grain (wheat) although in theory, any other suitable matrix would, with minor adaptations, be equally applicable.

Thin Layer Chromatography (TLC)

TLC was performed as described in Example 1.

High Performance Liquid Chromatography (HPLC)

HPLC analyses were conducted using the same equipment as described in Example 1. The solvent system consisted of acetonitrile and $H_2O$:

| Time | Acetonitrile | $H_2O$ |
|------|--------------|--------|
| 0    | 36           | 64     |
| 10   | 36           | 64     |
| 15   | 48           | 52     |
| 20   | 100          | 0      |
| 30   | 100          | 0      |

The flow rate was 1.0 mL/min.

A 25 g sample of bread wheat (composite sample Canadian Hard Red Winter Wheat) was finely ground in a coffee mill and 25 mg digitonin (Sigma Chemical Co., St. Louis, Mo.) thoroughly mixed in with, the grounds. The mixture was then carefully added with vigorous stirring to 125 mL (solids/liquids=1/5 w:v) of refluxing aqueous 80% acetone and extracted with stirring for a further 20 minutes. After cooling to. room temperature, the mixture was centrifuged (2830×g, 15 min.) and the supernatant decanted. The pellet was then resuspended in 125 mL of fresh aqueous 80% acetone, re-extracted twice and the combined supernatants, constituting the extract, evaporated in vacuo by rotary evaporation at 40° C. to an oily residue.

This extract was taken up in 5 mL of acidified aqueous 50% ethanol (ethanol:water:glacial acetic acid 50:49:1 v:v:v) and loaded onto a graduated glass column of Octyl Sepharose CL-4B™ gel, pre-equilibrated and gravity-packed (final packed $V_b$=100 mL; i.e. 4 mL gel/gm wheat extracted ) in the same acidified aqueous 50% ethanol solvent. The column was then washed with $3 \times V_b$ of acidified aqueous 50% ethanol to give a $K' \leq 3$ fraction which was concentrated in vacuo at 40° C. by rotary evaporation to a brownish syrup. TLC analyses showed this fraction contained digitonin, sugars, amino acids, organic acids, some of the pigments and some of the prolamines amongst others. The material remaining on the column was removed (and the column regenerated for re-use), by passing $3 \times V_b$ of 95% ethanol to give a $K' \geq 3$ fraction. TLC of this fraction revealed only traces of the digitonin and contained the bulk of the polar lipids, the lipophilic prolamine proteins, and some of the pigments, amongst others. The completeness of the separation of digitonin between the $K' \leq 3$ fraction and the $K' \geq 3$ fraction was examined by quantitative HPLC using an authentic sample of digitonin prepared and characterized (TLC, HPLC, MS) from the commercial sample. Greater than 96% of the digitonin was recovered in the $K' \leq 3$ fraction with less than 4% in the $K' \geq 3$ fraction.

Figure 3:
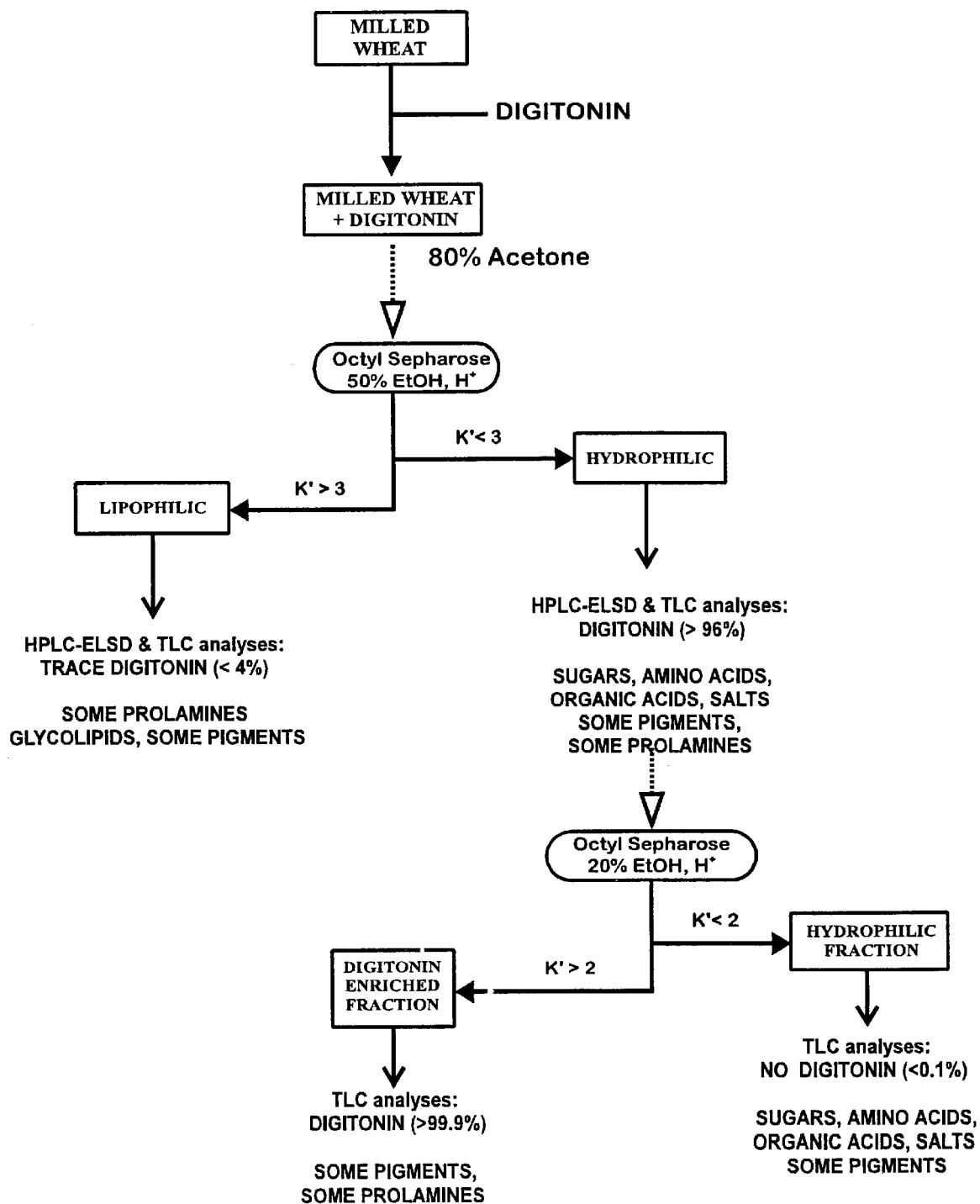
FIG. 3 shows the scheme for the isolation and purification of digitonin added to the wheat sample, as per Example 3.

Further purification of the digitonin in the $K' \leq 3$ fraction from other components was carried out using HIC simply by re-running the 50% ethanol $K' \leq 3$ fraction through the column using a solvent with a higher water content to increase the binding of the cardiac glycoside to the gel. Thus, the $K' \leq 3$ fraction was taken up in 5 mL of acidified aqueous 20% ethanol (ethanol:water:glacial acetic acid 50:49:1 v:v:v) and loaded onto a graduated glass column of Octyl Sepharose CL-4B™ gel, pre-equilibrated and gravity-packed (final packed $V_b$=100 mL; 4 mL gel/gm wheat extracted ) in the same acidified aqueous 20% ethanol solvent. The column was then washed with $2 \times V_b$ of acidified aqueous 20% ethanol to give a $K' \leq 2$ fraction containing the sugars, amino acids, and organic acids amongst others, which was concentrated in vacuo at 40° C. by rotary evaporation to a brownish syrup. The material remaining on the column was removed (and the column regenerated for re-use), by passing $2 \times V_b$ of 95% ethanol to give a $K' \geq 2$ fraction containing the digitonin, amongst others. The completeness of the separation of digitonin between the $K' \leq 2$ faction and the $K' \geq 2$ fraction was examined by quantitative TLC. The digitonin was found in the $K' \geq 2$ and no detectable digitonin occurred in the $K' \leq 2$ fraction. The scheme for the isolation and purification of digitonin added to the wheat sample is summarized in FIG. 3.

Example 4

Isolation and Purification of Nystatin from an Artificial Source by Hydrophobic Interaction Chromatography as an Example of the Recovery of a Drug from an Agricultural Crop which has been Genetically Transformed to Produce Antimicrobials.

Nystatin is an antifungal antibiotic produced by Streptomyces spp. (Merck Index #6834, E. Merck, 12th Edition, 1996). which has established itself in human therapy as a valuable agent for the treatment of both local and internal infections of molds and yeasts such as *Candida albicans*. It belongs to a group of macrocyclic lactone antibiotics containing a conjugated polyene system and a glycosidically-linked aminodesoxyhexose which, in combination with a free carboxylic group give the compound zwitterionic properties. A number of trade names are known including Fungicidin™ and Mycostatinm™. Although nystatin occurs in Streptomyces spp. and is normally extracted and purified from extracts of cultures of this bacterium, the use of genetically modified plants for the production of this drug represents an alternative that may prove economically more practical (from the standpoints of ease of cultivation, yield, storage, transport, etc.) than current practices. It is not the purpose of the current example to provide an economically practical alternative to these practices, but rather to illustrate the application of the technology described herein for the isolation and purification of the drug from model sources. To this end, the alternative model plant matrix system chosen was a cereal grain (wheat) although in theory, any other suitable matrix would, with minor adaptations, be equally applicable.

Nystatin was obtained from Sigma Chemical Co., St Louis, Mo. Sepharose™ and Sephadex™ based gels were obtained from Pharmacia. All solvents and reagents were of the highest purity commercially available.

Thin Layer Chromatography (TLC)

TLC was performed as described in Example 1.

A 25 g sample of bread wheat (composite sample Canadian Hard Red Winter Wheat) was finely ground in a coffee mill and 25 mg nystatin (Sigma Chemical Co., St. Louis, Mo.) thoroughly mixed in with the grounds. The mixture was then carefully added with vigorous stirring to 125 mL (solids/liquids=1/5 w:v) of refluxing acidified aqueous 80% ethanol (ethanol:water:glacial acetic acid 80:19:1 v:v:v) and extracted with stirring for a further 20 minutes. After cooling to room temperature, the mixture was centrifuged (2830×g, 15 min.) and the supernatant decanted. The pellet was then resuspended in 125 mL of fresh acidified aqueous 80% ethanol, re-extracted twice and the combined supernatants, constituting the extract, evaporated in vacuo by rotary evaporation at 40° C. to an oily residue.

This extract was taken up in 5 mL of acidified aqueous 50% ethanol (ethanol:water:glacial acetic acid 50:49:1 v:v:v) and loaded onto a graduated glass column of Octyl Sepharose CL-4B™ gel, prequilibrated and gravity-packed (final packed $V_b$=100 mL; i.e. 4 mL gel/gm wheat extracted) in the same acidified aqueous 50% ethanol solvent. The column was then washed with $3 \times V_b$ the acidified aqueous 50% ethanol to give a K'≦3 fraction which was concentrated in vacuo at 40° C. by rotary evaporation to a brownish syrup. TLC analyses showed this fraction contained nystatin, sugars, amino acids, organic acids, some of the pigments and some of the prolamines amongst others. The material remaining on the column was removed (and the column regenerated for re-use), by passing $2 \times V_b$ of aqueous 80% ethanol and $2 \times V_b$ of aqueous 95% ethanol. TLC of these fractions revealed no traces of the nystatin and contained the bulk of the polar lipids, the lipophilic prolamine proteins, and some of the pigments.

Further purification of the nystatin in the K'≦3 fraction from other components was carried out using HIC simply by re-running the 50% ethanol K'≦3 fraction through the column using a solvent with a higher water content to increase the binding of the nystatin to the gel. Thus, the K'≦3 fraction was taken up in 5 mL of aqueous 1% acetic acid and loaded onto a graduated glass column of Octyl Sepharose CL-4B™ gel, pre-equilibrated and gravity-packed (final packed $V_b$=100 mL; i.e. 4 mL gel/gm wheat extracted ) in the same solvent. The column was then washed with $2 \times V_b$ of 1% acetic acid to give a K'≦2 fraction which was concentrated in vacuo at 40° C. by rotary evaporation to a brownish syrup. The material remaining on the column was removed (and the column regenerated for re-use), by passing $2 \times V_b$ of 80% ethanol to give a K'≧2 fraction. Qualitative TLC analyses of the K'≦2 fraction showed it contained the sugars, amino acids, organic acids and some of the pigments. Similar analyses of the K'≧2 fraction revealed the presence of nystatin and some of the pigments amongst others. The completeness of the separation of nystatin between the K'≦2 fraction and the K'≧2 fraction was examined by quantitative TLC. All (i.e. >99.9%) of the nystatin was found in the K'≧2 and no detectable (i.e. <0.1%) nystatin occurred in the K'≦2 fraction.

Figure 4:
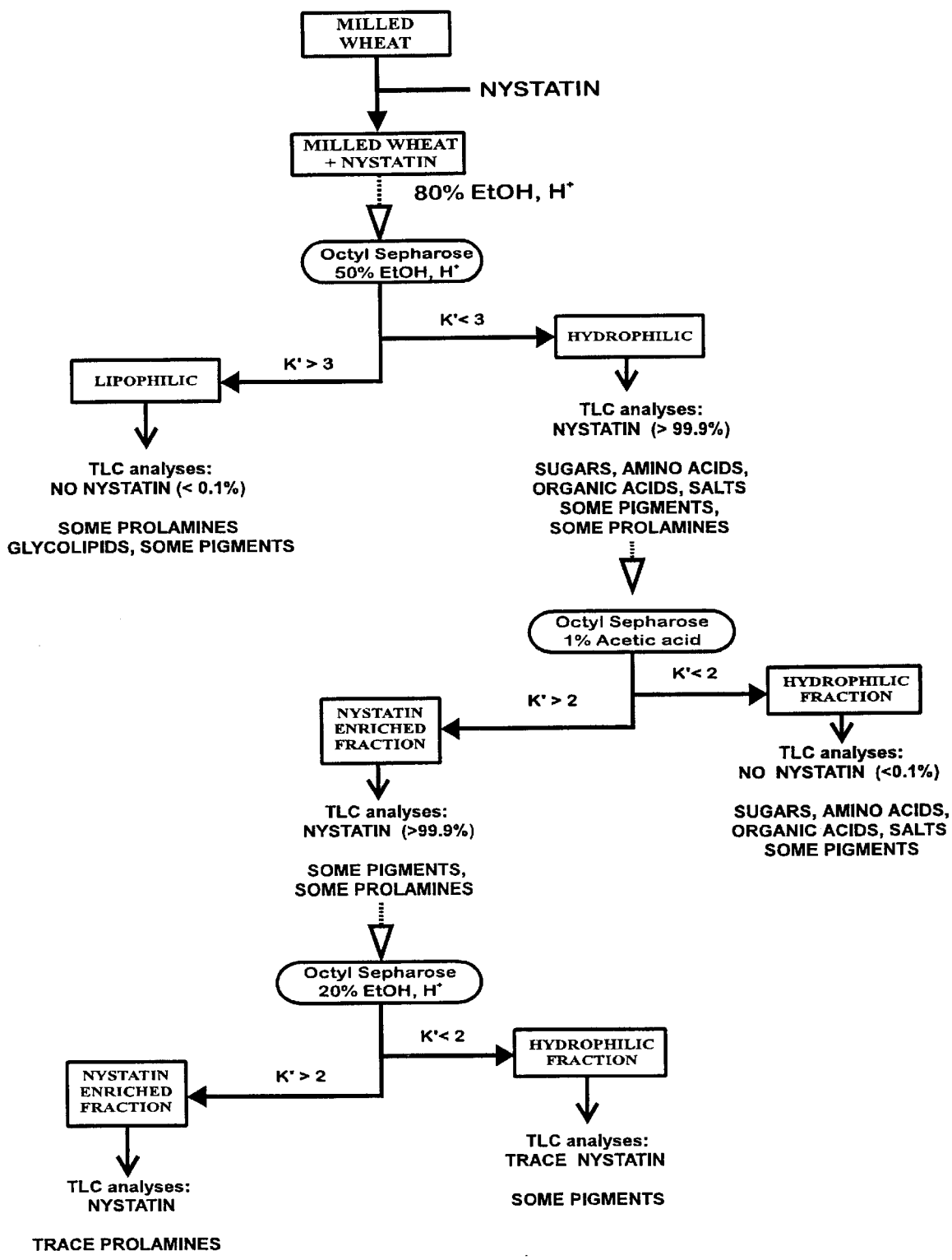
FIG. 4 shows the scheme for the isolation and purification of nystatin added to the wheat sample, as per Example 4.

Finally, still further purification of the nystatin was achieved HIC at an ethanol:water ratio intermediate between the above steps. Thus, the K'≧2 fraction was taken up in 5 mL of acidified aqueous 20% ethanol (ethanol:water:glacial acetic acid 20:79:.1 v:v:v) and loaded onto a graduated glass column of Octyl Sepharose CL-4B™ gel, preequilibrated and gravity-packed (final packed $V_b$ =100 mL; i.e. 4 mL gel/gm wheat extracted ) in the same solvent. The column was then washed with $2 \times V_b$ of acidified aqueous 20% ethanol to give a K'≦2 fraction which was concentrated in vacuo at 40° C. by rotary evaporation to a brownish syrup. The material remaining on the column was removed (and the column regenerated for re-use), by passing $2 \times V_b$ of 80% ethanol to give a K'≧2 fraction. Qualitative TLC analyses of the K'≦2 fraction showed it contained the remainder of the pigments but only traces of nystatin. The K'≧2 fraction, on the other hand, contained almost all of the nystatin in a highly purified form. The scheme for the isolation and purification of nystatin added to the wheat sample is summarized in FIG. 4.

Example 5
Isolation and Purification of Steryl Ferulates from Rice Bran Using Hydrophobic Interaction Chromatography on Octyl Sepharose CL-4B™

All procedures were carried out in subdued light to prevent the light-induced E-Z isomerization of the steryl ferulates. Rice bran was extracted with 95% ethanol by gradually adding, with vigorous stirring, 300 g of bran to 1.5 L (solids/liquid=1/5) of refluxing 95% ethanol and allowing the mixture to cool with continued stirring to approximately 4° C. The stirred mixture was then transferred to a volumetrically graduated 2 L glass funnel fitted with a coarse fritted disk and a stopcock. The slurry was left to equilibrate to room temperature and settle by gravity to give a packed bed and supernatant liquid extract of known volumes. The supernatant extract was drained and the packed bed washed with a further $2 \times V_b$ of fresh 95% ethanol The combined extract and washings were then concentrated in vacuo by rotary evaporation at 40° C. to an oily syrup. Further drying by lyophilization gave 27.54 g of yellow-green foam (yield: 9.18%).

A highly enriched steryl ferulate fraction was then prepared from the crude extract by Hydrophobic Interaction Chromatography on Octyl Sepharose CL-4B™ as follows: To the yellow-green foam, 125 mL Octyl Sepharose CL-4B™ pre-equilibrated in 95% ethanol was added and the mixture stirred to dissolve the syrupy extract and slurry the gel (adsorbing ratio:~13 mL gel /g extract or ~0.42 mL gel/g rice bran extracted). The slurried mixture was then concentrated in vacuo to remove as much of the solvent as possible, slurried again in aqueous 50% isopropanol and carefully added to a 500 mL volumetrically graduated column containing a 125 mL Octyl Sepharose CL-4B™ gel bed, pre-equilibrated and gravity-packed in aqueous 50% isopropanol. After settling, the combined absorbent gel layer and prepacked gel bed volume (i.e. $V_b$) was ~250 mL. The supernatant liquid above the newly constituted 250 mL gel bed was drawn off, the column washed with a further $2 \times V_b$ of fresh 50% aqueous ethanol, and the combined eluent and washings concentrated in vacuo to give a thick, yellow-brown resin by rotary evaporation at 40° C. The steryl ferulate-enriched fraction absorbed on the gel was then recovered with $2 \times V_b$ of 100% isopropanol.

Further purification of the steryl ferulates from other lipophilic compounds was achieved by double ion exchange chromatography using QAE Sephadex A-25™. Since the steryl ferulates have no net charge at or below pH 6, they will not be retained on an anion exchange matrix whereas lipids of the classes including free fatty acids, acidic phosphatides, amino acids, peptides, and phenolic acids will be retained and can thus be removed from the mixture. Furthermore, since the steryl ferulates have a net negative charge at or above pH 8, they will be retained on an anionic exchange matrix whereas all remaining neutral lipids will pass through the matrix. The retained steryl ferulates can then be recovered from the column by eluting the column with a mildly acidic recovery solution of pH 6 or less.

Accordingly, a volumetrically graduated column of QAE Sephadex A-25™ in the trifluoroacetate form was prepared by first converting 100 mL of the gel as received from the manufacturer in the Cl⁻ form, to the OH⁻ form with 1N NaOH in aqueous 50% ethanol, and then converting the OH⁻ form to the trifluoroacetate form with 1% trifluoroacetic acid in 50% ethanol (ethanol:water:trifluoroacetic acid 50:49:1). The column was then washed with aqueous 50% ethanol until the pH of the washings was ~6.Finally, the column was equilibrated in the solvent isopropanol:methanol dichloromethane:water (50:25:22.5:2.5 v:v:v:v), resuspended and allowed to settle to give a bed volume ($V_b$) of ~75 mL.

The steryl ferulate fraction prepared above was evaporated to dryness in vacuo by rotary evaporation at 40° C., and dissolved in 10 mL of isopropanol:methanol:dichloromethane:water (50:25:22.5:2.5 v:v:v:v). The solution was absorbed onto the column and washed with $2 \times V_b$ of fresh solvent to give a washing fraction highly enriched in the steryl ferulates amongst others. The anionic material adsorbed on the column, including free fatty acids, acidic phosphatides, amino acids, peptides, and phenolic acids was then recovered using $2 \times V_b$ of the solvent isopropanol:methanol:dichloromethane:5% aqueous trifluoroacetic acid (50:25:22.5:2.5 v:v:v:v), and the column recycled by washing the column and equilibrating to pH~6 using $2 \times V_b$ of isopropanol:methanol:dichloromethane:water (50:25:22.5:2.5 v:v:v:). The neutral washing fraction was concentrated to dryness in vacuo by rotary evaporation at 40° C. to give a yellowish-green oil, dissolved in 10 mL of isopropanol:methanol:dichloromethane:water (50:25:22.5:2.5 v:v:v:v), and absorbed onto a 75 mL $V_b$ QAE Sephadex A-25™ column in the OH⁻ form, prepared as described above and equilibrated in isopropanol:methanol:dichloromethane:water (50:25:22.5:2.5 v:v:v:v). The column was then washed with $2 \times V_b$ of fresh solvent to give a washing fraction consisting of, amongst others, neutral glycerides, wax alcohols and free and glycosylated sterols and their aliphatic esters. The absorbed material was recovered by passing $2 \times V_b$ of the solvent isopropanol:methanol:dichloromethane:5% aqueous acetic acid (50:25:22.5:2.5 v v:v:v), and concentrating the fraction in vacuo by rotary evaporation at 40° C. to give 1.17 g of a pale green foam containing >98% purity (HPLC, TLC, UV and MS) steryl ferulates (yield: 0.39% of dry bran extracted).

Figure 5:
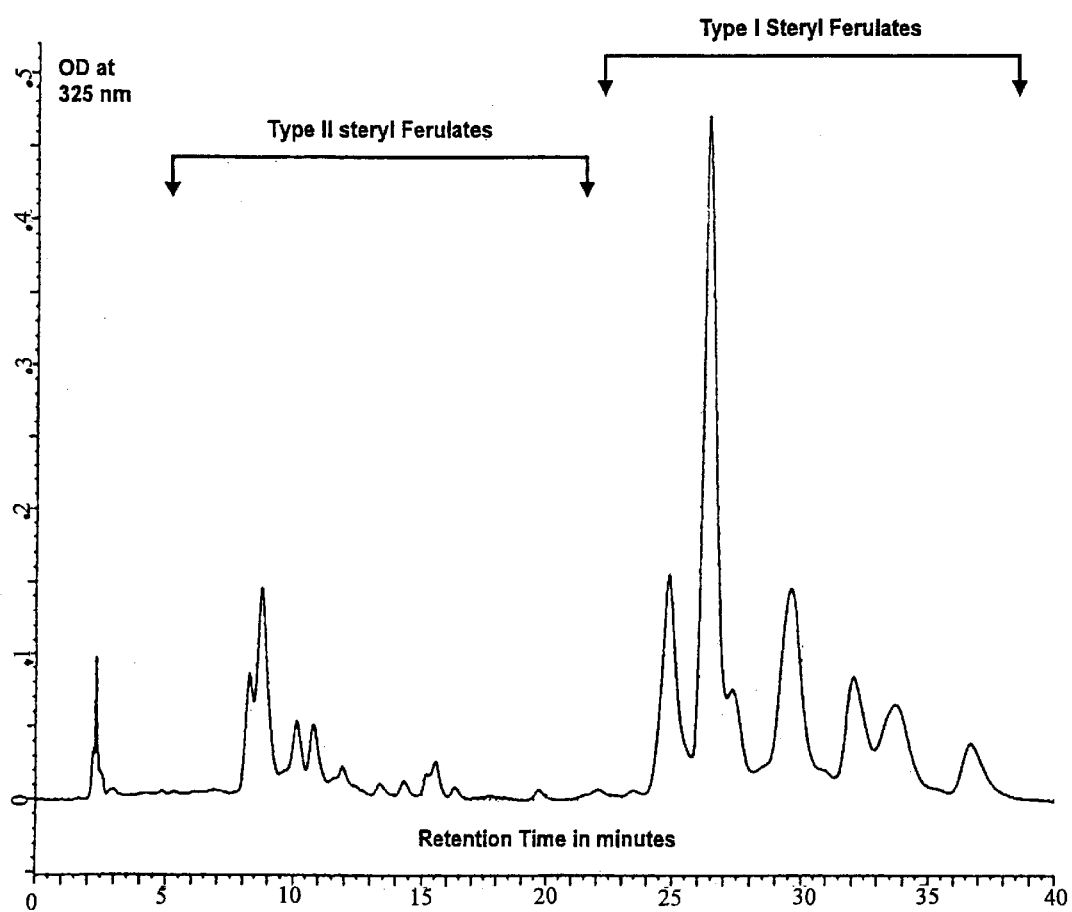
FIG. 5 is a typical HPLC tracing of a rice bran steryl ferulate mixture.

HPLC analysis of the steryl ferulate mixture showed the presence of at least 18 distinct components all of which exhibited the characteristic UV absorption spectrum of either an E- or Z-feruloyl moiety. A typical HPLC tracing of the mixture of steryl ferulates prepared above is shown in FIG. 5. To facilitate analyses, the mixture was arbitrarily separated into 2 types, Type I and Type II steryl ferulates, by further Hydrophobic Interaction Chromatography on Octyl Sepharose CL-4B™. The pale green foam prepared above (1.17 g) was dissolved in 15 mL of 95% ethanol and 40 mL of Octyl Sepharose CL-4B™, pre-equilibrated in 95% ethanol, added. After thorough mixing, the slurry was concentrated in vacuo by rotary evaporation at 40° C. to remove the ethanol, redispersed in 65% acetone, transferred with washings to a column of 85 mL Octyl Sepharose CL4B™ pre-equilibrated in 65% acetone, and allowed to settle by gravity (final $V_b$ 125 mL). The column was then washed with $3.5 \times V_b$ of fresh 65% acetone and the washings evaporated to dryness in vacua by rotary evaporation at 40° C., to give Type II steryl ferulates (0.018 g pale green foam; yield: 0.006% of dry bran extracted). The Type I steryl ferulates were then recovered from the column with $2 \times V_b$ isopropanol and evaporated to dryness in vacuao by rotary evaporation at 40° C., to give 0.972 g of pale green foam (yield: 0.32% of dry bran extracted).

The structural identification, qualitative and quantitative analyses of the rice bran steryl ferulate mixture were carried out on the Type I steryl ferulates, using the following methods:

High Performance Liquid Chromatography (HPLC):

Semi-preparative HPLC was carried out on a Beckman 110A pump fitted with a Rheodyne 7125 injector and a 200 µL sample loop. The HPLC was run in an isocratic mode with 100% methanol at 2.0 mL/min flow rate through a CSC ODS-2 column (10 µm, 9.4×250 mm). Injection volume was 50 µL(i.e. 8.4 mg) into the 200 µL sample loop. The eluent was monitored at 325 nm with a Hewlett-Packard 8452 diode array spectrophotometer.

Analytical runs were performed on a Thermo Separation Products P4000 quaternary pump fitted with a Rheodyne 7125 injector and 20 µL sample loop. Separations were effected on a CSC ODS-2 columnn (5 µm, 4.0×250 mm), using a mobile phase of methanol:acetonitrile:isopropanol:water (45:45:5:5 v:v:v:v) which was ramped to methanol:acetonitrile:isopropanol (45:50:5 v:v:v) from 6 to 10 minutes and held constant for 30 minutes. The flow rate was 1.0 mL/min and the temperature was maintained at 20° C. with a Varian 2080 column oven.

Thin-Layer Chromatography

Thin-layer chromatography was performed on both silica gel plates (Baker-Flex, 1B2-F), in the normal phase mode, with n-butyl acetate:cyclohexane (20:80 v:v) as solvent, and $C_{18}$ precoated plates (Whatman, MK $C_{18}F$, 200 µm) with 100% methanol as solvent. Steryl ferulates were visualized by examination of the plates under UV (365 nm) before and after spraying with a 5% solution of ethanolamine in isopropanol (v:v). The steryl ferulates were visible as dark UV-absorbing spots before spraying, turning sky blue with ethanolamine.

Specta Analyses

UV data was provided by a Waters 991 Photodiode Array Detector. NCI mass spectra were obtained using flow injection on a Hewlett Packard 1090 HPLC coupled to a 5988 HP mass spectrometer via a thermospray interface. EI mass spectra were acquired by direct inlet solid probe analysis on a Finnigan 4500 spectrometer with an ionization potential set to 30 eV. NMR spectra were acquired on a Bruker AM 500 spectrometer operating at 500 MHZ and 125.7 MHZ, respectively, for $^1H$ and $^{13}C$. Spectra were recorded in $CDCl_3$ and referenced to $CHCl_3$ at 7.24 ppm ($^1H$) and $CDCl_3$ at 77.0 ppm ($^{13}C$). All chemical shifts are reported relative to tetramethylsilane. $^1H$ assignments were aided by $^1H/^{13}C$ heteronuclear correlation spectra (HETCORR) and carbon resonance assignments by DEPT and HETCORR NMR experiments. Melting points were recorded on an Electrothermal apparatus and are uncorrected.

Quantitative Analyses

Quantization of the steryl ferulates was carried out on a Perkin Elmer LC-85B Spetrophotometric Detector monitoring at 326 nm with the attenuation set at 0.08 AU units and the detector response set at 20 ms. Integration was performed on Thermo Separations WOW software. Several standards of 24-methylenecycloartanol-3β-O-E-ferulate were prepared from material recrystallized from semi-preparative HPLC runs (colourless needles from aqueous isopropanol, mp: 193–194.5° C.) and used to construct a calibration curve. The response factor was applied to all types of steryl ferulates and consequently any concentrations were reported in terms of 24-methylenecycloartanol-3 β-O-E-ferulate equivalents. All standards and samples were stored at 4° C. in the dark and were stable for several months (no detectable indication of E/Z isomerization).

Figure 6:
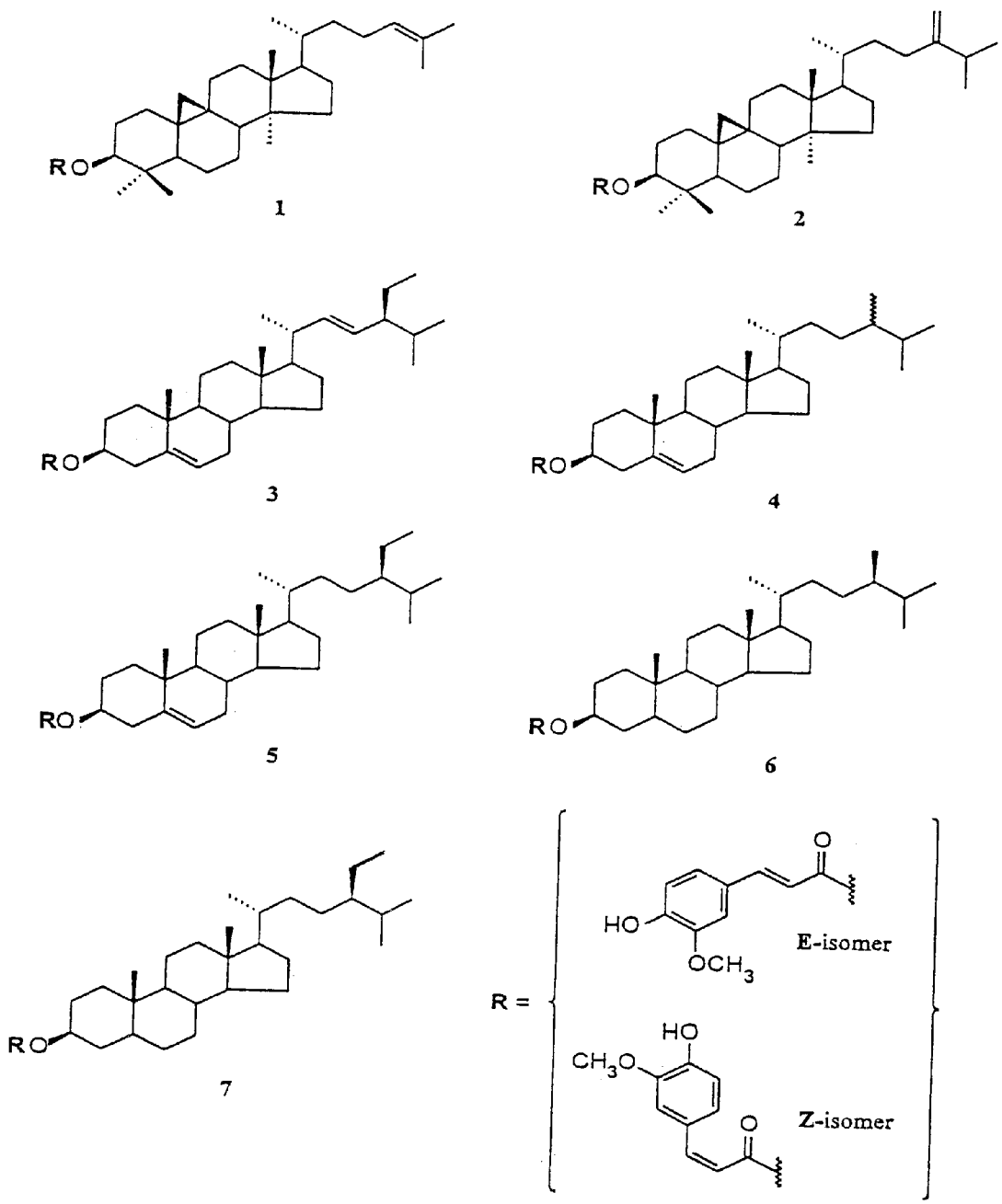
FIG. 6 shows the structures of Type I steryl ferulates isolated from rice bran.

Using repeated injections of the mixture of Type I steryl ferulates, individual components were isolated by semi-preparative HPLC and their purity monitored by analytical HPLC and TLC. When purified, pooled samples were concentrated in vacuo by rotary evaporation and crystallized from methanol. Sub-samples of each pure compound were dissolved in methanol:water (95:5 v:v) and exposed to UV light (365 mn) for 30 minutes in a Chromatovue chamber (Ultraviolet Products Ltd., Sacramento, Calif.) to induce E/Z isomerization and allow the production and characterization of both isomeric forms of each steryl ferulate. The identification, relative retention times ($RR_t$) and concentra tion of Type I steryl ferulates from the rice bran are summarized in Table 2 and their structures are shown in FIG. 6.

TABLE 2

Composition of Type I Steryl Ferulates from Rice Bran

| Compound | Structure | RR$_t$* | Concentration mg/100 g** |
|---|---|---|---|
| Cycloartenyl-E-ferulate | (IE) | 0.9434 | 34 |
| Cycloartenyl-Z-ferulate | (1Z) | 0.9718 | nd |
| 24-methylenecycloartanyl-E-ferulate | (2E) | 1.000 | 87 |
| 24-methylenecycloartanyl-Z-ferulate | (2Z) | 1.038 | 14 |
| Stigmasteryl-Z-ferulate | (3Z) | 1.076 | nd |
| 24ξ-methylcholesteryl-Z-ferulate | (4Z) | 1.088 | nd |
| Stigmasteryl-E-ferulate | (3E) | 1.110} | 49 |
| 24ξ-methylcholesteryl-E-ferulate | (4E) | 1.120} | |
| Sitosteryl-Z-ferulate | (5Z) | 1.180 | nd |
| Sitosteryl-E-ferulate | (5E) | 1.213 | 24 |
| Campestanyl-Z-ferulate | (6Z) | 1.229 | nd |
| Campestanyl-E-ferulate | (6E) | 1.272 | 26 |
| Stigmastanyl-Z-ferulate | (7Z) | 1.341 | 2 |
| Stigmastanyl-E-ferulate | (7E) | 1.388 | 13 |
| Total Type I steryl ferulates | | | 249 |

*Relative Retention Times (RR$_t$) relative to 24-methylenecycloartanol-E-ferulate (absolute retention time = 26.54 min)
**Concentration reported in 24-methylenecycloartanol-E-ferulate equivalents;
nd = not detected Preliminary analyses of the Type II steryl ferulates suggest that they are the more unsaturated analogues and isomers of the Type I ferulates containing one or two additional double bonds (e.g. cyclobranol) as seen by their mass spectra which exhibit comparable fragments at 2 and in some cases 4 mass units less than those exhibited by the Type I ferulates.

The use of Hydrophobic Interaction Chromatography on alkyl substituted polysaccharide gels for the separation of steryl ferulates offers an improved method when used in combination with ion-exchange chromatography for the preparation of these non-polar compounds over available methods. The porous nature of the polysaccharide gel matrix gives it a much higher loading capacity than conventional non-porous silica-based media. Typical loading values of 50–75 mg of crude extracts per mL of gel media represent an increase of from 10 to 50 fold over conventional products and are comparable to loading capacities of synthetic resins such as those based on modified polystyrene and polymethacrylate matrices (Takayanagi, H. et al., "Non-ionic adsorbents in separation processes" In, *Downstream Processing of Natural Products, A Practical Handbook*. Ed. by Michael S. Verall, John Wiley & Sons, Toronto, 1996. pp. 159–178).

Example 6
Isolation and Purification of Wheat Bran Flavonoids, 5-n-alk(en)ylresorcinols and Steryl Ferulates Using Hydrophobic Interaction Chromatography on Octyl Sepharose CL-4B™

Figure 7:
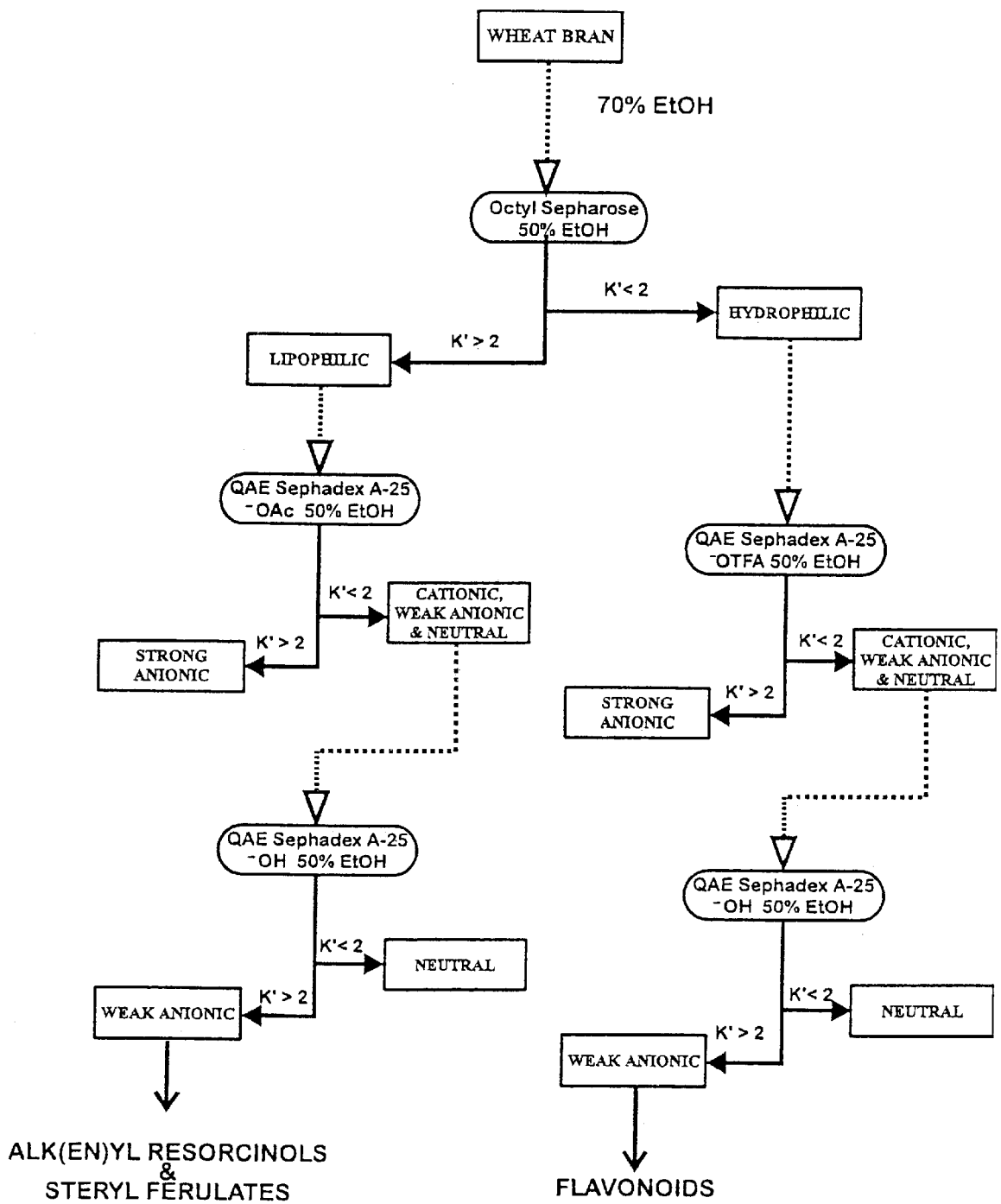
FIG. 7 shows the isolation, recovery and purification of wheat bran flavonoids, alk(en)ylresorcinols and steryl ferulates.

All extractions, fractionations and analyses were performed under subdued room lighting conditions with special attention paid to elimination of TV light from all solution chemistry to prevent the E-Z isomerization of the steryl ferulates. The isolation and purification procedure is summarized in FIG. 7. Wheat bran (composite sample, from light white wheat, "Product B ", E. Timm & Sons, Goole, U.K.) was ground in a Tekinar A-10 analytical mill for 20 seconds to reduce particle size to ≦400 mesh. To 100 mL refluxing aqueous 70% ethanol, 20 g of the wheat bran was carefully added with vigorous stirring (solids/liquids=1/5). With continued stirring the mixture was removed from the heat and allowed to extract for an additional 20 min., then poured into a volumetrically graduated column fitted with a polypropylene fritted disk of medium porosity. The column was then refrigerated at 4° C. in the dark and allowed to settle by gravity overnight. After re-equilibration to room temperature, the packed column of bed volume $V_b$ was drained of supernatant and washed with a further $3 \times V_b$ of fresh 70% ethanol. The extracted bed material was then removed from the column, resuspended in 100 mL boiling 70% ethanol, and the above extraction procedure repeated twice. The combined extracts and washings were combined, concentrated in vacuo by rotary evaporation at 40° C. to a yellow-brown syrup, (4.22 g; yield: 21.1%) and stored at −20° C. until further processed.

To isolate the non-polar constituents of interest, a steryl ferulate- and 5-n-alk(en)ylresorcinol-enriched fraction was prepared by Hydrophobic Interaction Chromatography using Octyl-Sepharose CL-4B™ as follows: To the yellow-brown syrup prepared above, 40 mL Octyl Sepharose CL-4B™ pre-equilibrated in 95% ethanol was added and the mixture stirred to dissolve the extract and slurry the gel (absorption ratio: ~10 mL gel/g extract or ~2 mL gel/g wheat bran extracted). The slurry was then concentrated in vacuo at 40° C. by rotary evaporation to remove as much of the solvent as possible, slurried again in aqueous 50% ethanol and carefully added to a 200 mL volumetrically graduated column containing a 60 mL Octyl Sepharose CL-4B™ gel bed, pre-equilibrated and gravity-packed in aqueous 25% ethanol. The gel bed was pre-equilibrated and packed in 25% rather than 50% ethanol to increase the density of the chromatography gel bed relative to the slurried extract-gel mixture to ensure proper gravity packing. After settling, the combined absorbent gel layer and prepacked gel bed volume (i.e. $V_b$) was ~100 mL. The supernatant liquid above the newly constituted 100 mL gel bed was drawn off, the column washed with a further $2 \times V_b$ of fresh aqueous 50% ethanol and the combined eluate and washings concentrated in vacuo at 40° C. by rotary evaporation to give a flavonoid-enriched hydrophilic fraction. The alk(en)ylresorcinol- and steryl ferulate-enriched hydrophobic fraction absorbed on the gel was then recovered with $2 \times V_b$ of 100% isopropanol.

Since the flavonoids present in the flavonoid-enriched hydrophilic fraction are uncharged at or below pH 6, they will not be retained on an anionic exchange matrix under these conditions. However, since the phenolic hydroxyl group(s) of flavonoids are negatively charged at or above pH 8, they will be retained at or above this pH. Accordingly, the hydrophilic fraction was further purified by the following double ion exchange chromatography on QAE Sephadex A-25™ anion exchange columns: First, treatment to remove non-flavonoid components such as anionic prolamines, peptides, and amino acids, organic acids and inorganic anions, all of which carry a net anionic charge at or below pH 6 was performed. A QAE Sephadex A-25™ anion exchange column was prepared essentially as described in Example 5 except it was converted from the hydroxyl form to the acetate form by passing an excess of 5% glacial acetic acid in aqueous 50% ethanol (ethanol:water:glacial acetic acid 50:45:5 v:v:v) through the column. The column was then equilibrated and washed with aqueous 50% ethanol until the pH of the washings was ~6. The flavonoid-enriched hydrophilic fraction prepared above was dissolved in ~10 mL 50% ethanol and absorbed onto the column. The column was then washed with $2 \times V_b$ of fresh aqueous 50% ethanol and the washing containing the flavonoids and other neutralicationic components of this sub-fraction evaporated to a thick, yellow glass. This sub-fraction was then redissolved in ~10 mL aqueous 50% ethanol. A QAE Sephadex A-25™ anion exchange column in the hydroxyl form was prepared essentially as described in Example 5. The sub-fraction was then added to the column and the column washed with a further $2 \times V_b$ of fresh aqueous 50% ethanol to give a neutral/cationic fraction devoid of flavonoids (HPLC, TLC). The flavonoids were then recovered from the column using the solvent ethanol:water:acetic acid 50:49:1 (v:v:v), concentrated to dryness in vacua at 40° C. and stored at −20° C. until further analyzed.

Using the same principles of selective ionization of phenolic OH groups at different pH values as described above for the flavonoids and the same protocols as described in Example 5, except that the trifluoracetate-form instead of the acetate-form, was used. The alk(en)ylresorcinol- and steryl ferulate-enriched lipophilic fraction was also further purified by double ion exchange chromatography on QAE Sephadex A-25™ in the trifluoroacetate and the hydroxyl forms. The recovered alk(en)ylresorcinol- and steryl ferulate- sub-fraction was concentrated in vacuo at 40° C. by rotary evaporation and stored at −20° C. until further analyzed The entire process for isolation, recovery and purification of the flavonoids, al(en)ylresorcinols and steryl ferulates from the wheat bran is summarized in FIG. 7.

The structural identification, qualitative and quantitative analyses of the flavonoids, alk(en)ylresorcinols and steryl ferulates were carried out using the following methods:

High Performance Liquid Chromatography (HPLC)

Semi-preparative HPLC was carried out on a Beckman 110A pump fitted with a Rheodyne 7125 injector and a 200 $\mu$L sample loop. The HPLC was run in an isocratic mode with 100% methanol at 2.0 mL/min flow rate through a CSC ODS-2 column (10 $\mu$m, 9.4×250 mm). Injection volume was 50 $\mu$L (i.e. 8.4 mg) into the 200 $\mu$L sample loop. The eluent was monitored at 325 nm for the steryl fenilates and 280 nm for the 5-n-alk(en)ylresorcinols with a Hewlett-Packard 8452 diode array spectrophotometer.

Analytical runs were performed on a Thermo Separation Products P4000 quaternary pump fitted with a Rheodyne 7125 injector and 20 $\mu$L sample loop. For both the 5-n-alk (en)ylresorcinols and the steryl ferulates, separations were effected on a CSC ODS-2 column (5 $\mu$m, 4.0×250 mm), using a mobile phase of methanol:acetonitrile:isopropanol:water (45:45:5:5 v:v:v:v) which was ramped to methanol:acetonitrile:isopropanol (45:50:5 v:v:v) from 6 to 10 minutes and held constant for 30 minutes. The flow rate was 1.0 mL/min and the temperature was maintained at 20° C. with a Varian 2080 column oven. For the flavonoids, analytical separations were carried out on a Hypersil ODS column (5 $\mu$m, 4.6×250 mm), using a mobile phase of acetonitrile and aqueous 2% acetic acid at a flow rate of 1.0 mL/min and the following gradient (v:v):

| Time | Acetonitrile | 2% Acetic Acid |
|---|---|---|
| 0 | 9 | 91 |
| 15 | 15 | 85 |
| 25 | 15 | 85 |
| 35 | 30 | 70 |
| 45 | 30 | 70 |
| 47 | 80 | 20 |
| 50 | 9 | 91 |

Thin-Layer Chromatography

Thin-layer chromatography of steryl ferulates and 5-n-alk (en)ylresorcinols was performed on both silica gel plates (Baker-Flex, IB2-F), in the normal phase mode, with n-butyl acetate:cyclohexane (20:80 v:v) as solvent, and $C_{18}$ pre-coated plates (Whatman, MK $C_{18}F$, 200 $\mu$m) with 100% methanol as solvent. Steryl ferulates were visualized by examination of the plates under UV (365 nm) before and after spraying with a 5% solution of ethanolamine in isopropanol. The steryl ferulates were visible as dark UV-absorbing spots before spraying, turning sky blue with ethanolamine. The 5-n-alk(en)ylresorcinols were visualised as brick red spots with the p-anisaldehyde spray reagent described in Example 1.

Thin-layer chromatography of the flavonoids was carried out on silica gel plates (Baker-Flex, 1B2-F), in the normal phase mode, using the solvent system: $CH_2Cl_2$:ethyl acetate-:methanol:aqueous 5%acetic acid 40:35:20:5 (v:v:v:v), and visualized by examination of the plate under UV light (365 nm) before and after spraying with a solution of 5% ethanolamine in isopropanol. Specific flavonoids gave yellow-green fluorescent colors characteristic of their structure and substitution patterns.

Spectral Analyses

UV data was provided by a Waters 991 Photodiode Array Detector. NCI mass spectra were obtained using flow injection on a Hewlett Packard 1090 HPLC coupled to a 5988 HP mass spectrometer via a thermospray interface. E mass spectra were acquired by direct inlet solid probe analysis on a Finnigan 4500 spectrometer with an ionization potential set to 30 eV. NMR spectra were acquired on a Bruker AM 500 spectrometer operating at 500 MHZ and 125.7 MHZ, respectively, for $^1H$ and $^{13}C$. Spectra were recorded in $CDCl_3$ (steryl ferulates and alk(en)ylresorcinols) or DMSO-$d_6$ (flavonoids) and referenced to $CHCl_3$ at 7.24 ppm ($^1H$) and $CDCl_3$ at 77.0 ppm ($^{13}C$). $^1H$ assignments were aided by $^1H/^{13}C$ heteronuclear correlation spectra (HETCORR) and carbon resonance assignments by DEPT and HETCORR NMR experiments. Melting points were recorded on an Electrothermal apparatus and are uncorrected.

Quantitative Analyses

Quantization of the steryl ferulates was carried out as described in Example 5. The response factor was applied to all types of steryl ferulates and consequently any concentrations are reported in terms of 24-methylenecycloartanol-3β-O-E-ferulate equivalents. Quantisation of the 5-n-alk(en) ylresorcinols was similarly carried out using 5-n-pentadecylresorcinol (Aldrich Chemical Co., Milwaukee, Wis.) as standard and preparing the calibration curve based on 280 nm absorptivity. Quantisation of flavonoids was recorded as flavone di-C-glycoside equivalents, based on a response calibration curve prepared with a crystalline standard of Apigenin6C-α-L-arabinofuranosyl-8C-β-D-pyranosylgalactoside obtained from wheat germ (Collins, F. W. and D'Attilio, R. Z., Cereal Foods.World 41: 586, 1996). All standards and samples were stored at 4° C. in the dark and were stable for several months (no detectable indication of E/Z isomerization or auto-oxidation).

Figure 8A:
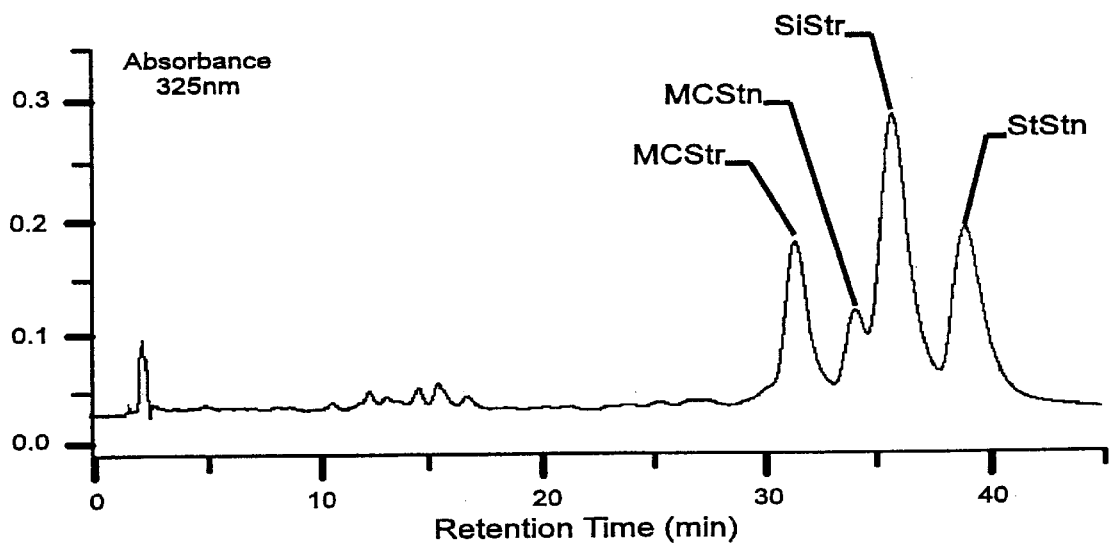
FIG. 8A depicts the HPLC profile of wheat bran steryl ferulates.
Figure 8B:
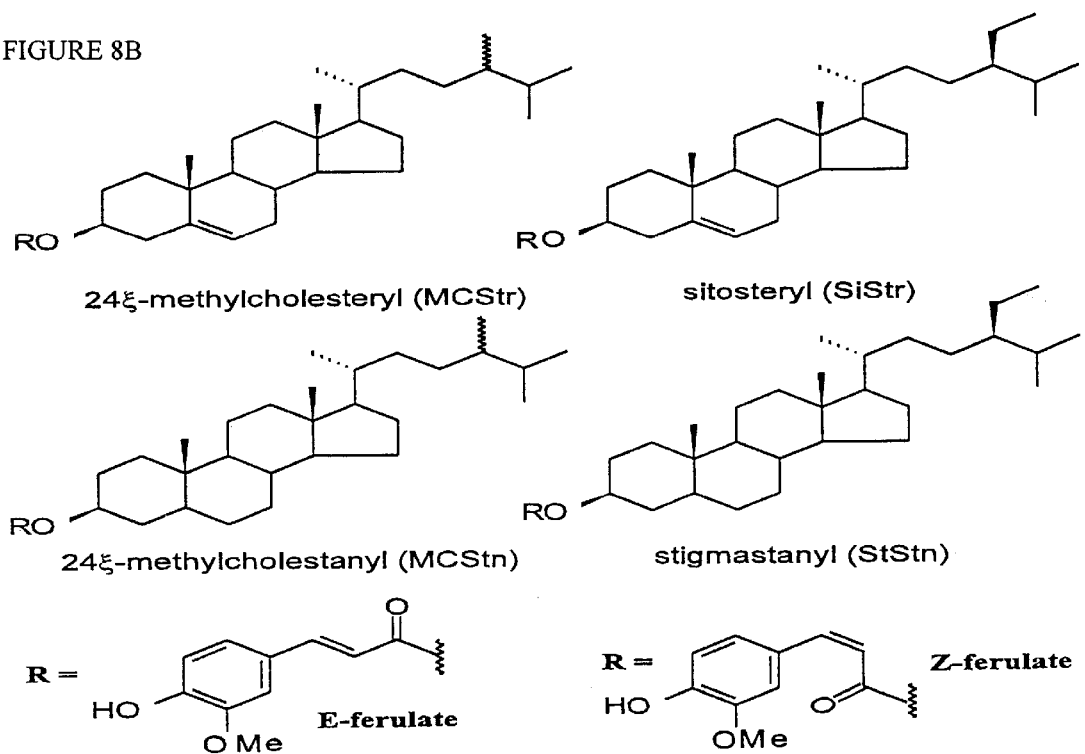
FIG. 8B depicts the structures of wheat bran steryl ferulates.

A typical HPLC profile of the mixture of steryl ferulates prepared from the wheat bran is shown in FIG. 8A. Structural identification of the individual components was made by cohromatography (HPLC, TLC) and comparison of spectral data (UV, MS, NMR) with authentic standards. Unlike the rice bran extracts (FIG. 6), only Type II steryl ferulates (FIG. 8B) were observed in the wheat bran extracts. In all, 4 major steryl ferulates were identified. The major component identified was the E-isomer of sitosteryl ferulate (SiStr), followed by the E-isomer of stigmastanyl ferulate (StStn). Lesser relative levels of both 24ξ-methylcholesteryl (MCStr) and 24ξ-methylcholestanyl (MCStn) ferulates in the E-forms were also detected. When exposed to light and moisture, all these ferulates undergo reversible isomerization (to various degrees depending on the individual compound involved and the conditions of light, pH, aqueous hydration etc.) and a mixture of both E- and Z-isomers can be encountered. However, no Z-isomers of the individual ferulates were detected under the preparation and storage conditions used in this example.

The results of the quantitative analyses of individual steryl ferulates are summarized in Table 3. When expressed as 24-methylenecycloartenol, the total quantity of steryl ferulates was 58.4 mg/100 gm of wheat bran, or 584 ppm (dry basis).

Figure 9A:
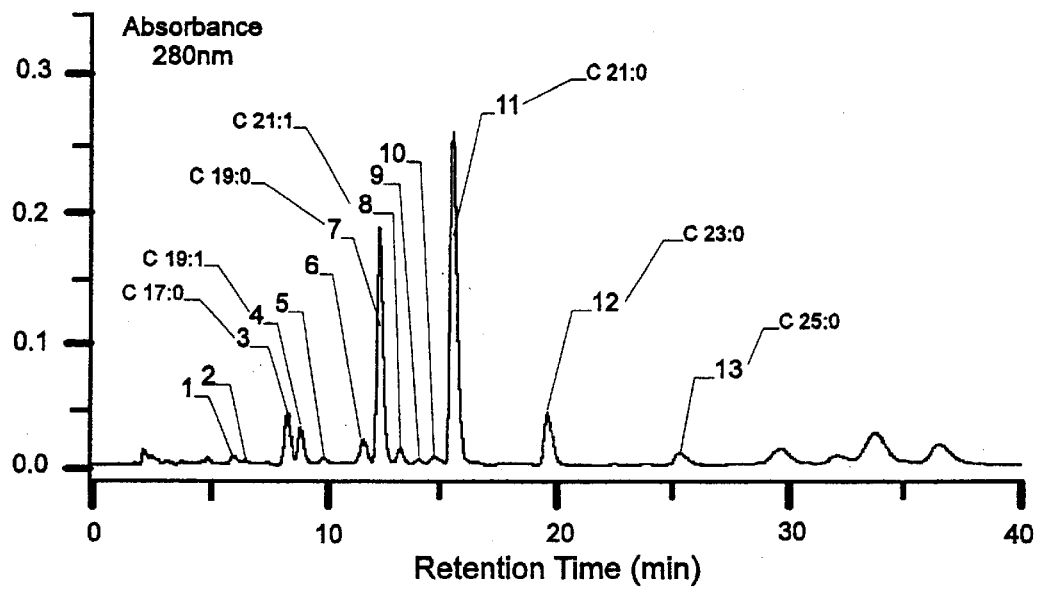
FIG. 9A shows the HPLC profile of 5-n-alk(en)ylresorcinols from wheat bran.
Figure 9B:
FIG. 9B shows example structures of 5-n-alk(en)ylresorcinols from wheat bran.
Figure 9B:
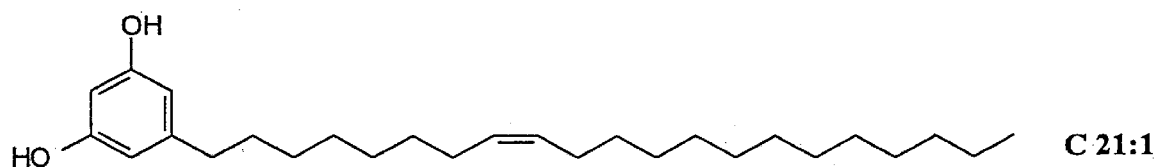

The 5-n-alk(en)ylresorcinol HPLC showed the presence of at least 13 peaks 12 of which were identified as members of this group of phenolic antioxidants. Individual components of the group were identified as described by Collins, P. W. and Mullin, W. J., J. Food Comp. Anal. 4: 270–275, 1991. An HPLC profile of the alk(en)ylresorcinol mixture from the wheat bran is shown in FIG. 9A, along with the identity of major components and structural examples (FIG. 9B). The structural examples indicate the position of attachment of the allyl or alkenyl function represented by the abbreviation used in the HPLC profile (e.g. C 17:0, C 21:1 etc.). The results of the quantitative analysis are summarized in Table 4. The profile was dominated by 3 major components (peak #7, #11 and #12, FIG. 9A) in the homologous series containing n-alkyl side chains of 19, 21 and 23 carbons. Lesser amounts of the corresponding mono- and di-unsaturated analogues were also present. As shown in Table 3, the total amount of 5-n-alk(en)ylresorcinols in the wheat bran sample, calculated by summation and expressed as the 5-n-pentadecylresorcinol equivalents, was about 600 mg/gm of bran extracted or 6,000 ppm (dry basis).

Since the steryl ferulates and 5-n-alk(en)ylresorcinols were not group separated from each other in this example, the overall purity of each group could not be evaluated directly by comparing the spectrophotometric quantisation with the gravimetric quantisation for each fraction. Nevertheless, based on summation of the UV data of the combined fractions with the total weight of the lipophilic sub-fraction used in the spectrophotometric quantisations (Tables 3 and 4), overall purity was estimated at over 95% with respect to these 2 groups of compounds.

Figure 10A:
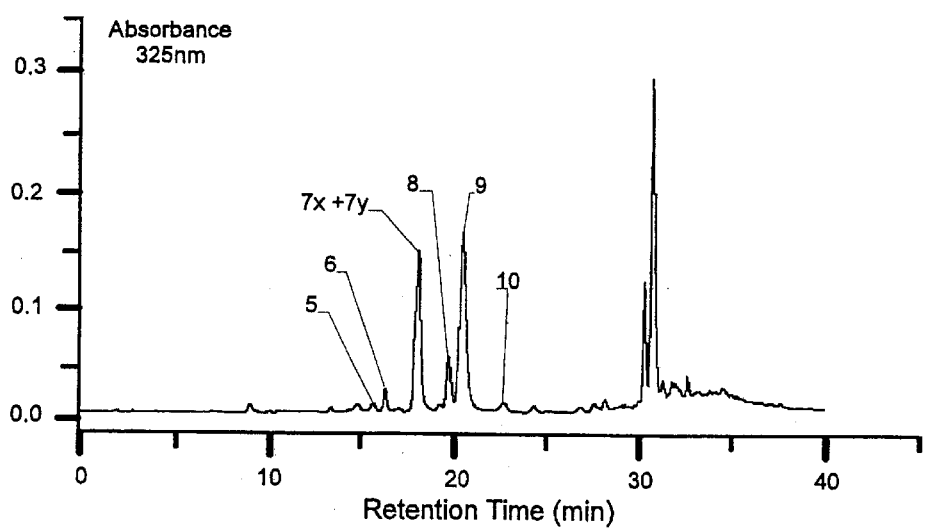
FIG. 10A shows the HPLC profile of major flavonoids of wheat bran.
Figure 10B:
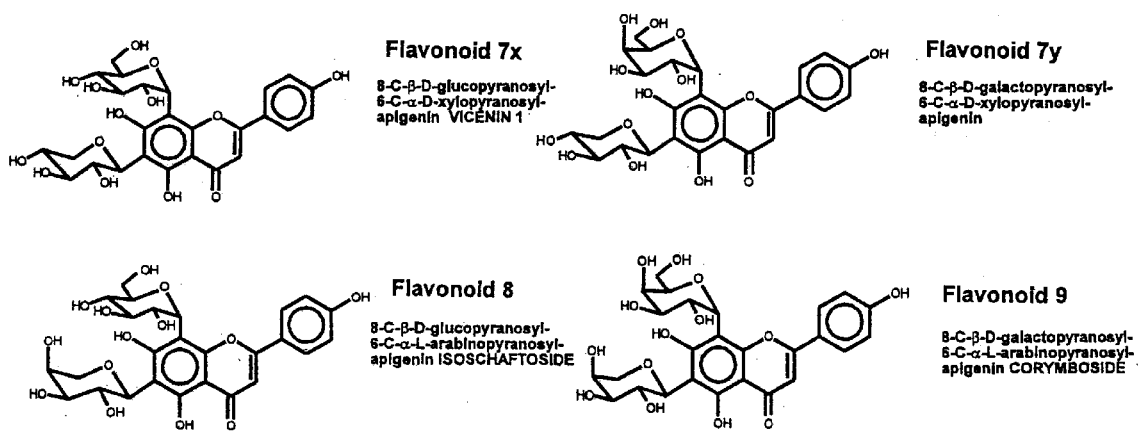
FIG. 10B shows the structures of major flavonoids of wheat bran.

The results of the flavonoid HPLC analysis areshown in FIG. 10A, along with the structures of the major components of the mixture (FIG. 10B). The 4 major glycosides identified (HPLC, TLC, NMR, MS) included: 7 x (Vicenin I), 7y (8-C-β-D-galactopyranosyl -6-C-α-xylopyranosyl-apigenin), 8, {8-β-D-glucopyranosyl-α-L-arabinosoyl-apigenin (Isoshaftoside)}, and 9, {8-β-D-galactopyranosyl-α-L-arabinosyl-apigenin (Corymboside)}. Although 7x and 7y were not separated in the profile shown, they were detected in other HPLC systems. A number of other flavonoids were detected and monitored but their structures have not been confirmed. These included flavonoids 5, 6 and 10. Total flavonoids expressed as mg equivalents of flavonoid 9 was 2.0 mg/100 gm or 20 ppm (dry basis).

TABLE 3

Composition of Type I Steryl Ferulates from Wheat Bran

| Compound | $RR_t$* | Concentration mg/100 g** |
|---|---|---|
| 24ξ-methylcholesteryl-Z-ferulate | 1.088 | nd |
| 24ξ-methylcholesteryl-E-ferulate | 1.110 | 12.0 |

TABLE 3-continued

Composition of Type I Steryl Ferulates from Wheat Bran

| Compound | $RR_t$* | Concentration mg/100 g** |
|---|---|---|
| 24ξ-methylcholestanyl-Z-ferulate | 1.186 | nd |
| 24ξ-methylcholestanyl-E-ferulate | 1.210 | 24.7 |
| Sitosteryl-Z-ferulate | 1.234 | nd |
| Sitosteryl-E-ferulate | 1.268 | 5.4 |
| Stigmastanyl-Z-ferulate | 1.341 | nd |
| Stigmastanyl-E-ferulate | 1.388 | 16.3 |
| Total Type I steryl ferulates | | 58.4 |

*Relative Retention Times ($RR_t$) relative to 24-methylenecycloartanol-E-ferulate (absolute retention time = 28.10 min)
**Concentration reported in 24-methylenecycloartanol-E-ferulate equivalents;
nd not detected

TABLE 4

Composition of 5-n-alk(en)ylresorcinols from Wheat Bran

| Peak No. | 5-n-Substituent | $RR_t$* | Concentration mg/100 g** |
|---|---|---|---|
| 1 | C 15:0 | 1.000 | 5.9 |
| 2 | C 19:2 | 1.113 | 1.7 |
| 3 | C 17:0 | 1.270 | nd |
| 4 | C 19:1 | 1.327 | 28.4 |
| 5 | C 21:2 | 1.434 | 4.0 |
| 6 | C 21:1 | 1.523 | 20.1 |
| 7 | C 19:0 | 1.531 | 178.8 |
| 8 | C 23:1 | 1.866 | 9.8 |
| 9 | | 1.988 | nd |
| 10 | C 25:1 | 2.104 | nd |
| 11 | C 21:0 | 2.187 | 276.3 |
| 12 | C 23:0 | 2.790 | 54.5 |
| 13 | C 25:0 | 3.658 | 19.3 |
| Total 5-n-alk(en)ylresorcinols | | | 598.4 |

*Relative Retention Times ($RR_t$) relative to 5-n-pentadecylresorcinol (absolute retention time = 6.63 min)
**Concentration reported in 5-n-pentadecylresorcinol equivalents
nd not determined All scientific publications and patent documents are incorporated herein by reference.

The present invention has been described with regard to preferred embodiments. However, it will be understood to persons skilled in the art that a number of variations and modifications can be made without departing from the scope of the invention as described in the following claims.

The embodiments of the invention in which an exclusive Property of privilege is claimed are defined as follows:

1. A method of isolating a non-polar extractive comprising:
    contacting said non-polar extractive in an aqueous organic solvent solution with an aliphatic-substituted polysaccharide gel matrix;
    washing said gel matrix with said aqueous organic solvent solution;
    washing said gel matrix with additional aqueous organic solvent solution, wherein the proportion of the organic solvent in said additional solution is increased; and
    recovering said extractives from an effluent stream.

2. The method of claim 1, further comprising regenerating the gel matrix for re-use.

3. The method according to claim 1, wherein the non-polar plant extractives are selected from the group consisting of steroids and triterpenoids, flavonoids, phenolic conjugates, polar lipids, and prolamines.

4. The method according to claim 3, wherein the steroids and triterpenoids are selected from the group consisting of saponins, cardiac glycosides and steryl conjugates.

5. The method according to claim 3, wherein the flavonoids are selected from the group consisting of flavones, flavonols, isoflavones and all of their glycosides.

6. The method according to claim 3, wherein the phenolic conjugates are selected from the group consisting of aliphatic alcohols, esters and amides.

7. The method according to claim 3, wherein the polar lipids are selected from the group consisting of mono- and di-glycerides and their derivates and alk(en)yl resorcinols.

8. The method according to claim 3, wherein the prolamines are selected from the group consisting of zein, avenin, hordein and gliadin.

9. The method according to claim 1, wherein the non-polar extractives are from either synthetic or natural source.

10. The method according to claim 9, wherein the natural source of the non-polar extractives is selected from the group consisting of plant material, algae, fungi and unicellular organisms.

11. The method according to claim 10, wherein the plant material is selected from the group consisting of agricultural, viniculture, horticulture, aquaculture and plants native to lands and oceans.

12. The method according to claim 11, wherein the agricultural plant material is selected from the group consisting of wheat, oats, rye, corn, rice, quinoa, amaranth, buckwheat, triticale or barley; or oilseeds, such as soybean, canola, flaxseed, sunflower, safflower or mustard; or pulse crops, for example, peas, lentils or beans; or forage crops, such as fescue, timothy, clover, alfalfa or wheatgrass; or herbs, such as parsley, rosemary, sage or mint.

13. The method according to claim 1, wherein the organic solvent solution is a solution containing a lower alcohol, a ketone or a combination thereof.

14. The method according to claim 13, wherein the lower alcohol is selected from the group consisting of methanol, ethanol, propanol and isopropanol.

15. The method according to claim 13, wherein the ketone is acetone.

16. The method according to claim 1, wherein the gel matrix consist of a neutral polysaccharide gel matrix of the polyanhydrogalactan class, a neutral polysaccharide gel matrix of the polydextran class or a neutral polysaccharide gel matrix of the hydroxpropyl polydextran class.

17. The method according to claim 16, wherein the gel matrix contains covalently linked alkyl substitution of from 4 carbon (ie butyl) to 8 carbon (ie octyl) functions at a 4% or more substitution rate, stable in neutral and mildly acidic or alkaline solutions of said aqueous organic solvent solution, with a molecular size exclusion cut-off range equal to or greater than 10,000 Daltons.

18. The method according to claim 17, wherein the substitution rate is from 4% to 8%.

19. The method according to claim 18, wherein the substitution rate is from 4% to 6%.

20. The method according to claim 18, wherein the gel matrix is Octyl Sepharose CL-4B™ gel.

* * * * *